United States Patent
Brack et al.

(10) Patent No.: US 7,968,685 B2
(45) Date of Patent: Jun. 28, 2011

(54) ANTIBODIES AGAINST TENASCIN-C

(75) Inventors: Simon Brack, Zurich (CH); Michela Silacci, Zurich (CH); Dario Neri, Buchs (CH)

(73) Assignee: Philogen S.p.A., Siena (IT)

( * ) Notice: Subject to any disclaimer, the term of this patent is extended or adjusted under 35 U.S.C. 154(b) by 853 days.

(21) Appl. No.: 11/718,919

(22) PCT Filed: Oct. 31, 2005

(86) PCT No.: PCT/EP2005/011624
§ 371 (c)(1),
(2), (4) Date: Oct. 1, 2007

(87) PCT Pub. No.: WO2006/050834
PCT Pub. Date: May 18, 2006

(65) Prior Publication Data
US 2008/0056997 A1    Mar. 6, 2008

Related U.S. Application Data

(60) Provisional application No. 60/626,173, filed on Nov. 9, 2004, provisional application No. 60/677,376, filed on May 3, 2005.

(51) Int. Cl.
*A61K 39/00* (2006.01)
(52) U.S. Cl. .................... 530/387.1; 424/130.1
(58) Field of Classification Search .................... None
See application file for complete search history.

(56) References Cited

FOREIGN PATENT DOCUMENTS
WO    WO 00/63699    10/2000
WO    WO 01/62800    8/2001

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Occhino et al. (Int. J. Mol. Med., vol. 14(3), pp. 383-388, Sep. 14, 2004) Abstract only.*
B. Carnemolla et al., "Identification of a Glioblastoma-Associated Tenascin-C Isoform by a High Affinity Recombinant Antibody", American Journal of Pathology, 154: 1345-1352 (1999).
A. Merlo et al., "Biodistribution of 111In-Labelled SCN-bz-DTPA-BC-2 Mab Following Loco-Regional Injection into Glioblastomas", Int. J. Cancer, 71: 810-816 (1997).
M. Latinjnhouwers et al., "Expression of tenascin-C splice variants by human skin cells", Arch. Dermatol. Res., 292: 446-454 (2000).
C.G. Davis et al., "Transgenic mice as a source of fully human antibodies for the treatment of cancer", Cancer and Metastasis Reviews, 18: 421-425 (1999).
H.R. Hoogenboom, "Overview of Antibody Phase-Display Technology and Its Applications", Methods in Molecular Biology, 178: 1-37 (2002).
A. Desiderio et al., "A Semi-synthetic Repertoire of Intrinsically Stable Antibody Fragments Derived from a Single-framework Scaffold", J. Mol. Biol. 310: 603-615 (2001).
M. Silacci et al., "Design, construction, and characterization of a large synthetic human antibody phage display library", Proteomics, 5: 2340-2350 (2005).
A. Pini et al., "Design and Use of a Phage Display Library", The Journal of Biological Chemistry, 273: 21769-21776 (1998).
Balza, E., et al. "Production and characterization of monoclonal antibodies specific for different epitopes of human tenascin." FEBS Lett. Oct. 11, 1993;332(1-2):39-43.
Murphy-Ullrich, J.E., et al. "Focal adhesion integrity is downregulated by the alternatively spliced domain of human tenascin." J Cell Biol. Nov. 1991;115(4):1127-36.
Hauck, M.L., et al. "The effects of clinically relevant hyperthermic temperatures on the kinetic binding parameters of a monoclonal antibody." Nucl Med Biol. May 1996;23(4):551-7.
Reardon, D.A., et al. "Phase II trial of murine (131)I-labeled antitenascin monoclonal antibody 81C6 administered into surgically created resection cavities of patients with newly diagnosed malignant gliomas." J Clin Oncol. Mar. 1, 2002;20(5):1389-97.

* cited by examiner

*Primary Examiner* — Laura B Goddard
*Assistant Examiner* — Meera Natarajan
(74) *Attorney, Agent, or Firm* — Dann, Dorfman, Herrell & Skillman; Kathleen D. Rigaut; Patrick J. Hagan

(57) ABSTRACT

Specific binding members against extracellular matrix protein tenascin-C, especially scFv antibody molecules against domain A1, domain C and domain D of tenascin-C. Anti-tenascin-C specific binding members conjugated with labels, cytotoxic molecules or cytokines. Use of anti-tenascin-C specific binding members in diagnosis and treatment, especially of cancer.

14 Claims, 5 Drawing Sheets

ANTIBODIES AGAINST TENASCIN-C

CROSS-REFERENCE TO RELATED APPLICATIONS

This application is the U.S. National Stage of International Application No. PCT/EP2005/011624, filed 31 Oct. 2005, which claims priority from U.S. Provisional Applications Nos. 60/626,173, filed 9 Nov. 2004 and 60/677,376, filed 3 May 2005. The disclosures of the aforesaid applications are incorporated by reference in their entireties in the present application.

The present invention relates to specific binding members directed to tenascin-C, in particular human antibodies against human tenascin-C. These specific binding members have a range of therapeutic applications, for example in the diagnosis and treatment of cancer.

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumorigenesis or angiogenesis.

The schematic domain structure of tenascin-C is depicted in FIG. 1. Several isoforms of tenascin-C can be generated as a result of alternative splicing which may lead to the inclusion of (multiple) domains in the central part of this protein, ranging from domain A1 to domain D [Borsi L et al *Int J Cancer* 1992; 52:688-692, Carnemolla B et al. *Eur J Biochem* 1992; 205:561-567]. It had previously been assumed that domains A1-D could be inserted or omitted "in block" in the tenascin-C molecule by a mechanism of alternative spicing, leading to "tenascin-C large" and "tenascin-C small" molecules [Borsi L et al *J Biol Chem* 1995; 270:6243-6245]. A strong over-expression of the large isoform of tenascin-C has been reported for a number of tumors [Borsi 1992 supra], and two monoclonal antibodies specific for domains A1 and D, respectively, have been extensively characterized in the clinic [Riva P et al. *Int J Cancer* 1992; 51:7-13, Riva P et al. *Cancer Res* 1995; 55:5952s-5956s, Paganelli G et al *Eur J Nucl Med* 1994; 21:314-321, Reardon D A et al. *J Clin Oncol* 2002; 20:1389-1397, Bigner D D et al. *J Clin Oncol* 1998; 16:2202-2212.

However, it has recently become clear that a more complex regulation of the alternative splicing mechanism takes place, leading to an increased molecular heterogeneity among the large isoforms of tenascin-C. For example, it has been reported that the extra domain C of tenascin-C displays a more restricted pattern of expression compared with the other alternatively spliced domains of tenascin-C [Carnemolla B et al. *Am J Pathol* 1999; 154:1345-1352], with a predominantly perivascular staining as depicted with immunohistochemistry. The C domain of tenascin-C is undetectable in most normal adult tissues, but is over-expressed in high-grade astrocytomas [Carnemolla B et al. *Am J Pathol* 1999; 154: 1345-1352] and other tumor types. Further support for the heterogeneity between large tenascin-C isoforms comes from transcriptional analyses, which confirmed that large tenascin-C transcripts feature a heterogeneous composition [Katenkamp K et al. *J Pathol* 2004; 203:771-779]. An additional level of complexity is provided by the presence or absence of post-translational modifications (e.g. glycosylation), which may modify certain epitopes on the surface of individual protein domains and make them unavailable to a specific molecular recognition in vitro or in vivo to specific monoclonal antibodies.

Even though the rapid isolation of antibodies specific to virtually any protein of interest can be accomplished with existing methodologies in vitro, it is not obvious that such antibodies recognize the epitope in biological specimens or in animal models of disease. Possible reasons for lack of binding in vivo include post-translational modifications of the epitope, masking of the epitope and insufficient antibody specificity or stability. It is therefore difficult to assess the suitability of monoclonal antibodies for practical applications based solely on their reactivity with recombinant antigens (or antigen fragments) in typical solid-phase assays, such as enzyme-linked immunosorbent assays (ELISA), which are routinely used for the screening of monoclonal antibodies.

Monoclonal antibodies to the individual domains of the tenascin-C large isoforms therefore need to be analyzed individually, in order to evaluate their suitability for diagnostic and therapeutic applications.

The present inventors have isolated human monoclonal antibody fragments specific to different epitopes within the alternatively spliced region of tenascin-C. These antibodies are characterized by their ability to recognize large tenascin-C isoforms in biological specimens, as well as by a highly specific binding in ELISA assays, with a striking differentiation among closely related antigens.

An aspect of the invention provides a specific binding member which binds human tenascin-C, in particular tenascin-C large isoform.

Preferred specific binding members are tumour specific and bind preferentially to tumour tissue relative to normal tissue. Specific binding members may, for example, bind to stroma and/or neo- and peri-vascular structures of tumour tissue preferentially to normal tissue.

A specific binding member may bind preferentially to tenascin-C large isoform relative to tenascin-C small isoform.

In some embodiments, the specific binding member may bind to the A1 domain of tenascin-C. A suitable specific binding member may comprise;
  an antibody VH domain selected from the group consisting of the 4A1-F16 VH domain of SEQ ID NO. 2, the 3A1-D5 VH domain of SEQ ID NO. 12 and a VH domain comprising one or more VH CDR's with an amino acid sequence selected from SEQ ID NO. 5, SEQ ID NO. 6, SEQ ID NO. 7 and SEQ ID NO: 13; and/or
  an antibody VL domain selected from the group consisting of the VL domain of SEQ ID NO. 4 or SEQ ID NO: 49), and a VL domain comprising one or more VL CDR's with an amino acid sequence selected from SEQ ID NO. 8, SEQ ID NO. 9 and SEQ ID NO. 10.

4A1-F16 is also referred to herein as F16.

For example, a suitable specific binding member may comprise the 4A1-F16/3A1-D5 VL domain of SEQ ID NO. 4 or SEQ ID NO: 49 and/or the 4A1-F16 VH domain of SEQ ID NO. 2 or the 3A1-D5 VH domain of SEQ ID NO: 12.

In other embodiments, the specific binding member may bind to the C domain of tenascin-C. A suitable specific binding member may comprise;
  an antibody VH domain selected from the group consisting of the E10 VH domain (SEQ ID NO. 15 or SEQ ID NO: 48), the A12 VH domain (SEQ ID NO. 25), the F4 and G11 VH domain (SEQ ID NO: 29 or SEQ ID NO: 45) and a VH domain comprising one or more VH CDR's with an amino acid sequence selected from SEQ ID NO. 18, SEQ ID NO. 19, SEQ ID NO. 20, SEQ ID NO. 26 and SEQ ID NO. 27; and/or
  an antibody VL domain selected from the group consisting of the VL domain of SEQ ID NO. 17 or SEQ ID NO 81, the F4 VL domain with the amino acid sequence of SEQ ID NO: 31 or SEQ ID NO: 83, the G11 VL domain with the amino acid sequence of SEQ ID NO: 35 or SEQ ID NO: 47, and a VL domain comprising one or more VL CDR's with an amino acid sequence selected from SEQ ID NO: 21, SEQ ID NO: 22, SEQ ID NO: 23, SEQ ID NO: 32 and SEQ ID NO: 33.

Thus in one example, the specific binding member may comprise;
an antibody VH domain selected from the group consisting of the E10 VH domain (SEQ ID NO. 15 or SEQ ID NO: 48), the A12 VH domain (SEQ ID NO: 25) and a VH domain comprising one or more VH CDR's with an amino acid sequence selected from SEQ ID NO. 18, SEQ ID NO. 19, SEQ ID NO. 20, SEQ ID NO. 26 and SEQ ID NO. 27; and/or
an antibody VL domain selected from the group consisting of the VL domain of SEQ ID NO. 17 or SEQ ID NO: 81, and a VL domain comprising one or more VL CDR's with an amino acid sequence selected from SEQ ID NO: 21, SEQ ID NO: 22 and SEQ ID NO: 23.

For example, a suitable specific binding member may comprise the E10/A12 VL domain of SEQ ID NO. 17 or SEQ ID NO: 81 and/or the E10 VH domain of SEQ ID NO: 15 or SEQ ID NO: 48) or the A12 VH domain of SEQ ID NO: 25.

In another example, the specific binding member may comprise:
an antibody VH domain selected from the group consisting of the F4 and G11 VH domain (SEQ ID NO: 29 or SEQ ID NO: 45) and a VH domain comprising one or more VH CDRs with an amino acid sequence selected from SEQ ID NO: 18, SEQ ID NO: 19 and SEQ ID NO: 20; and/or
an antibody VL domain selected from the group consisting of the F4 VL domain (SEQ ID NO: 31 or SEQ ID NO: 83), the G11 VL domain (SEQ ID NO: 35 or SEQ ID NO: 47) and a VL domain comprising one or more VL CDRs with an amino acid sequence selected from SEQ ID NO: 32, SEQ ID NO: 33, SEQ ID NO: 22 and SEQ ID NO: 23.

For example, a suitable specific binding member may comprise the F4/G11 VH domain of SEQ ID NO: 29 or SEQ ID NO: 45 and/or the F4 VL domain of SEQ ID NO: 31 or SEQ ID NO: 83 or the G11 VL domain of SEQ ID NO: 35 or SEQ ID NO: 47.

In another embodiment, the specific binding member binds to domain D of tenascin C. Preferably the specific binding member binds to the human domain D. It may cross-react with the mouse isoform. We isolated antibody molecules specific for domain D. The original clone is designated F4S. We also developed an affinity matured variant of F4S, designated D11. We further developed an affinity matured variant of D11, designated P12.

Accordingly, a suitable specific binding member may comprise
an antibody VH domain selected from the group consisting of the F4S VH domain of SEQ ID NO. 58, the D11 VH domain of SEQ ID NO. 55, the P12 VH domain of SEQ ID NO: 52 and a VH domain comprising one or more VH CDRs with an amino acid sequence selected from SEQ ID NO. 61, SEQ ID NO. 62, SEQ ID NO. 63, SEQ ID NO. 64, SEQ ID NO: 65 and SEQ ID NO: 66; and/or
an antibody VL domain selected from the group consisting of the P12 and D11 VL domain of SEQ ID NO. 53, the F4S VL domain of SEQ ID NO. 60, and a VL domain comprising one or more VL CDRs with an amino acid sequence selected from SEQ ID NO. 67, SEQ ID NO. 68, SEQ ID NO: 69, SEQ ID NO: 70 and SEQ ID NO. 71.

Generally, a VH domain is paired with a VL domain to provide an antibody antigen-binding site, although as discussed further below, a VH domain alone may be used to bind antigen. In one preferred embodiment, a VH domain described herein (i.e. SEQ ID NOS 2, 12, 15, 25, 29, 45, 48, 52, 56, or 58) is paired with the corresponding VL domain (i.e. SEQ ID NO: 4 or SEQ ID NO: 50 (for 4A1-F16 and 3A1-D5), SEQ ID NO: 17 or SEQ ID NO: 81 (for A12 and E10), SEQ ID NO: 31, SEQ ID NO: 83, SEQ ID NO: 35 or SEQ ID NO: 47 for F4 and G11), SEQ ID NO: 54 for P12 and D11, or SEQ ID NO: 60 for F4S, so that an antibody antigen-binding site is formed comprising both the VH and VL domains (e.g. a site comprising both the 4A1-F16 VH and VL domains, 3A1-D5 VH and VL domains, E10 VH and VL domains, A12 VH and VL domains, F4 VH and VL domains, G11 VH and VL domains, P12 VH and VL domains, D11 VH and VL domains or F4S VH and VL domains). In other embodiments, a VH domain may paired with a VL domain other than the corresponding VL domain, preferably a VL domain from a specific binding member that binds the same domain of tenascin-C. Light-chain promiscuity is well established in the art.

One or more CDRs may be taken from a VH or VL domain as disclosed herein and incorporated into a suitable framework. This is discussed further below. CDRs are generally defined as per Kabat. Preferably a VH domain and/or a VL domain comprises a CDR1, a CDR2 and a CDR3. 4A1-F16 VH CDR1 is shown in SEQ ID NO: 5. 3A1-D5 VH CDR1 is shown in SEQ ID NO: 13. 4A1-F16 and 3A1-D5 VH CDRs 2 and 3 are shown in SEQ ID NOS 6 and 7, respectively. 4A1-F16 and 3A1-D5 VL CDR's 1, 2 and 3 are shown in SEQ ID NOS 8, 9 and 10, respectively. E10 VH CDRs 1 and 2 are shown in SEQ ID NOS 18 and 19. A12 VH CDRs 1 and 2 are shown in SEQ ID NOS 26 and 27. E10 and A12 VH CDR3 is shown in SEQ ID NO: 23. E10 and A12 VL CDR's 1, 2 and 3 are shown in SEQ ID NOS: 21, 22 and 23, respectively. F4 and G11 VH CDRs 1, 2 and 3 are shown in SEQ ID NOS: 18, 19 and 20, respectively. F4 VL CDRs 1, 2 and 3 are shown in SEQ ID NOS: 32, 33 and 23, respectively. G11 VL CDRs 1, 2 and 3 are shown in SEQ ID NOS: 32, 22 and 23, respectively. P12 VH CDRs are shown in SEQ ID NOS: 61, 63 and 66, respectively. P12 VL CDRs are shown in SEQ ID NOS: 67, 69 and 71, respectively. D11 VH CDRs are SEQ ID NOS: 62, 64 and 66, respectively. D11 VL CDRs are SEQ ID NOS: 67, 69 and 71, respectively. F4S VH CDRs are SEQ ID NOS: 62, 65 and 66, respectively. F4S VL CDRs are SEQ ID NOS: 68, 70 and 71, respectively.

In some embodiments, a specific binding member may comprise an antibody VH domain comprising one or more of a CDR3 with the amino acid sequence of SEQ ID NO. 7, a CDR2 with the amino acid sequence of SEQ ID NO. 6, and a CDR1 with the amino acid sequence of SEQ ID NO. 5 or, more preferably, SEQ ID NO. 13.

In other embodiments, a specific binding member may comprise an antibody VH domain comprising one or more of a CDR3 with the amino acid sequence of SEQ ID NO: 20, a CDR2 with the amino acid sequence of SEQ ID NO: 27 or, more preferably, SEQ ID NO: 19, and a CDR1 with the amino acid sequence of SEQ ID NO: 26 or, more preferably, SEQ ID NO: 18.

A specific binding member may comprise an antibody VL domain comprising one or more of a CDR3 with the amino acid sequence of SEQ ID NO: 23, a CDR2 with the amino acid sequence of SEQ ID NO: 22 or SEQ ID NO: 33, and a CDR1 with the amino acid sequence of SEQ ID NO: 21 or SEQ ID NO: 32.

Preferably the specific binding member is an scFv, as described in more detail elsewhere herein. The VH and VL domains may be joined through a peptide linker, for example a linker having an amino acid sequence as set out in SEQ ID NO: 37. Normally, the linker has an amino acid sequence comprising one or more tandem repeats of a motif. Typically the motif is a five residue sequence, and preferably at least 4 of the residues are Gly or Ser. Where four of the five residues is Gly or Ser, the other residue may be Ala. More preferably each of the five residues is Gly or Ser. Preferred motifs are GGGGS, SSSSG, GSGSA and GGSGG (SEQ ID NOS: 76, 77, 78 and 79, respectively). Preferably, the motifs are adjacent in the sequence, with no intervening nucleotides between the repeats. The linker sequence may comprise or consist of between one and five, preferably three or four, repeats of the motif. For example, a linker with three tandem repeats may have one of the following amino acid sequences:

```
GGGGSGGGGSGGGGS - SEQ ID NO:39

SSSSGSSSSGSSSSG - SEQ ID NO:41

GSGSAGSGSAGSGSA - SEQ ID NO:42

GGSGGGGSGGGSGG - SEQ ID NO:43.
```

Variants of the VH and VL domains and CDRs of which the sequences are set out herein and which can be employed in specific binding members for tenascin-C can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDRs. In particular, alterations may be made in VH CDR1, VH CDR2 and/or VH CDR3, especially VH CDR3.

A specific binding member according to the invention may be one which competes for binding to antigen with any specific binding member which both binds Tenescin-C large isoform, in particular the A1 or C domains thereof, and comprises a specific binding member, VH and/or VL domain disclosed herein, or VH CDR disclosed herein, or variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, a further aspect of the present invention provides a specific binding member comprising a human antibody antigen-binding site which competes with one or more of 4A1-F16, 3A1-D5, E10, A12, F4, G11, P12, D11 and F4S for binding to tenascin-C.

Various methods are available in the art for obtaining antibodies against tenascin-C large isoform which may compete with 4A1-F16, 3A1-D5, E10, A12, F4 G11, P12, D11 or F4S. Preferably, such antibodies bind preferentially to tenascin-C large isoform relative to tenascin-C small isoform.

In a further aspect, the present invention provides a method of obtaining one or-more specific binding members able to bind the antigen, the method including bringing into contact a library of specific binding members according to the invention and said antigen, and selecting one or more specific binding members of the library able to bind said antigen.

The library may be displayed on the surface of bacteriophage particles, each particle containing nucleic acid encoding the antibody VH variable domain displayed on its surface, and optionally also a displayed VL domain if present.

Following selection of specific binding members able to bind the antigen and displayed on bacteriophage particles, nucleic acid may be taken from a bacteriophage particle displaying a said selected specific binding member. Such nucleic acid may be used in subsequent production of a specific binding member or an antibody VH variable domain (optionally an antibody VL variable domain) by expression from nucleic acid with the sequence of nucleic acid taken from a bacteriophage particle displaying a said selected specific binding member.

An antibody VH variable domain with the amino acid sequence of an antibody VH variable domain of a said selected specific binding member may be provided in isolated form, as may a specific binding member comprising such a VH domain.

Ability to bind tenascin-C may be further tested, also ability to compete with 4A1-F16, 3A1-D5, E10, A12, F4, G11, P12, D11 or F4S for binding to tenascin-C.

A specific binding member according to the present invention may bind tenascin-C with the affinity of one or more of 4A1-F16, 3A1-D5, E10, A12, F4, G11, P12, D11 or F4S or with a greater or lesser affinity.

Binding affinity of different specific binding members can be compared under appropriate conditions.

In addition to antibody sequences, a specific binding member according to the present invention may comprise other amino acids, e.g. forming a peptide or polypeptide, such as a folded domain, or to impart to the molecule another functional characteristic in addition to ability to bind antigen.

Specific binding members of the invention may carry a detectable label, for example an agent which facilitates tumor detection such as a radionuclide or fluorophore, or may be conjugated to an agent capable of triggering a biocidal event, such as a radionuclide, photosensitizer, drug, cytokine, procoagulant factor, toxin or enzyme (e.g. via a peptidyl bond or linker), for use in a method of therapy.

In further aspects, the invention provides an isolated nucleic acid which comprises a sequence encoding a specific binding member, VH or VL domains according to the present invention, and methods of preparing a specific binding member, a VH domain and/or a VL domain of the invention, which comprise expressing said nucleic acid under conditions to bring about production of said specific binding member, VH domain and/or VL domain, and recovering it.

Specific binding members described herein may be used in a method of treatment or diagnosis of the human or animal body, such as a method of treatment (which may include prophylactic treatment) of a disease or disorder, in particular a proliferative disorder such as cancer, in a human patient which comprises administering to said patient an effective amount of a specific binding member.

A further aspect of the present invention provides nucleic acid, generally isolated, encoding an antibody VH variable domain and/or VL variable domain disclosed herein.

Another aspect of the present invention provides nucleic acid, generally isolated, encoding a VH CDR or VL CDR sequence disclosed herein, especially a VH CDR selected from SEQ ID NOS 5, 6, 7, 13, 18, 19, 20, 26 and 27 or a VL CDR selected from SEQ ID NOS 8, 9, 10, 21, 22, 23, 32 and 33.

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and specific binding members comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Terminology

Specific Binding Member

This describes a member of a pair of molecules that have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is substantially homologous to, an antibody binding domain. Examples of antibodies are the immunoglobulin isotypes and their isotypic subclasses; fragments which comprise an antigen binding domain such as Fab, scFv, Fv, dAb, Fd; and diabodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilized by the incorporation of disulphide bridges linking the VH and VL domains (Y. Reiter et al. Nature Biotech 14 1239-1245 1996). Minibodies comprising an scFv joined to a CH3 domain may also be made (S. Hu et al, Cancer Res. 56 3055-3061 1996).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al, Protein Eng. 9 616-621, 1996).

Antigen Binding Domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain).

Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). For example, an antibody specific for Tenascin-C may show little or no binding to other components of the extracellular matrix such as fibronectin. Similarly, an antibody specific for Tenascin-C large isoform may show little or no binding to Tenascin-C small isoform. The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members, will be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NSO (ECACC 85110503) cells, or they may be (for example if produced by expression in a prokaryotic cell) unglycosylated.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, substitutions may be made in the CDR and/or VH or VL domain.

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu)).

Preferably, a CDR amino acid sequence substantially as set out herein is carried as a CDR in a human variable domain or a substantial portion thereof.

Variable domains employed in the invention may be obtained from any germline or rearranged human variable domain, or may be a synthetic variable domain based on consensus sequences of known human variable domains. A CDR sequence of the invention (e.g. CDR1, CDR2 or CDR3) may be introduced into a repertoire of variable domains lacking a CDR (e.g. the corresponding CDR1, CDR2 or CDR3), using recombinant DNA technology.

For example, Marks et al (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR-derived sequences of the present invention may be shuffled with repertoires of VH or VL domains lacking a CDR, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature*, 1994, 370:389-391), who describes the technique in relation to a β-lactamase gene but observes that the approach may be used for the generation of antibodies.

A further alternative is to generate novel VH or VL regions carrying CDR-derived sequences of the invention using random mutagenesis of one or more selected VH and/or VL genes to generate mutations within the entire variable domain. Such a technique is described by Gram et al (1992, *Proc. Natl. Acad. Sci. USA*, 89:3576-3580), who used error-prone PCR.

Another method which may be used is to direct mutagenesis to CDR regions of VH or VL genes. Such techniques are disclosed by Barbas et al, (1994, *Proc. Natl. Acad. Sci., USA*, 91:3809-3813) and Schier et al (1996, *J. Mol. Biol.* 263:551-567).

All the above-described techniques are known as such in the art and in themselves do not form part of the present invention. The skilled person will be able to use such techniques to provide specific binding members of the invention using routine methodology in the art.

A further aspect of the invention provides a method for obtaining an antibody antigen binding domain specific for tenascin-C, the method comprising providing, by way of addition, deletion, substitution or insertion of one or more amino acids in the amino acid sequence of a VH domain set out herein, a VH domain which is an amino acid sequence variant of the VH domain, optionally combining the VH domain thus provided with one or more VL domains, and testing the VH domain or VH/VL combination or combinations for to identify a specific binding member or an antibody antigen binding domain specific for tenascin-C. Said VL domain may have an amino acid sequence which is substantially as set out herein.

In some embodiments, the one or more amino acids may added, deleted, substituted or inserted into one or more CDRs of the VH domain, for example CDR1, CDR2 and/or CDR3.

An analogous method may be employed comprising providing, by way of addition, deletion, substitution or insertion of one or more amino acids in the amino acid sequence of a VL domain set out herein, a VL domain which is an amino acid sequence variant of the VL domain, combining the VL domain thus provided with one or more VH domains, and testing the VH/VL combination or combinations for to identify a specific binding member or an antibody antigen binding domain specific for tenascin-C. Said VH domain may have an amino acid sequence which is substantially as set out herein or may be an amino acid sequence variant of a VH domain which is substantially as set out herein obtained as described above.

In some embodiments, the one or more amino acids may added, deleted, substituted or inserted into one or more CDRs of the VL domain.

A further aspect of the invention provides a method of preparing a specific binding member specific for tenascin-C, which method comprises:

(a) providing a starting repertoire of nucleic acids encoding a VH domain which either include a CDR to be replaced or lack a CDR encoding region;

(b) combining said repertoire with a donor nucleic acid encoding an amino acid sequence substantially as set out herein for a VH CDR such that said donor nucleic acid is inserted into the CDR region in the repertoire, so as to provide a product repertoire of nucleic acids encoding a VH domain;

(c) expressing the nucleic acids of said product repertoire;

(d) selecting a specific binding member specific for a tenascin-C antigen; and (e) recovering said specific binding member or nucleic acid encoding it.

The CDR may be a VH CDR1, CDR2 or CDR3.

Again, an analogous method may be employed in which a VL CDR of the invention is combined with a repertoire of nucleic acids encoding a VL domain which either include a CDR to be replaced or lack a CDR encoding region.

The CDR may be a VL CDR1, CDR2 or CDR3.

Similarly, one or more, or all three CDRs may be grafted into a repertoire of VH or VL domains that are then screened for a specific binding member or specific binding members specific for tenascin-C, in particular tenascin-C large isoforms.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of NB or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single chain specific binding domains, these domains may be used to screen for complementary domains capable of forming a two-domain specific binding member able to bind tenascin-C.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, a VL domain may be attached at its C-terminal end to antibody light chain constant domains including human Cκ or Cλ chains, preferably Cλ chains. Similarly, a specific binding member based on a VH domain may be attached at its C-terminal end to all or part of an immunoglobulin heavy chain derived from any antibody isotype, e.g. IgG, IgA, IgE and IgM and any of the isotype sub-classes, particularly IgG1 and IgG4.

Specific binding members of the invention may be labelled with a detectable or functional label.

Detectable labels may include radionuclides, such as iodine-131, yttrium-90, indium-111 and technicium-99, which may be attached to antibodies of the invention using conventional chemistry known in the art of antibody imaging. A specific binding member labelled with a radioactive isotope may be used to selectively deliver radiation to a specific target, such as a tumour. This may be useful in imaging the tumour or in delivering a cytoxic dose of radiation, as described below.

Other detectable labels may include enzyme labels such as horseradish peroxidase, chemical moieties such as biotin which may be detected via binding to a specific cognate detectable moiety, e.g. labelled avidin, fluorochromes such as fluorescein, rhodamine, phycoerythrin and Texas Red and near infrared fluorophores, including cyanine dye derivatives such as Cy7 (Amersham Pharmacia) and Alexa750 (Molecular probes).

In other embodiments, a detectable label may comprise a microbubble derivative, which is detectable by ultrasound (Joseph S et al Pharm Res. 2004 June; 21(6):920-6), or a magnetic particle (Schellenberger E A et al. Bioconjug. Chem. 2004 September-October; 15(5): 1062-7).

A functional label may include an agent which is capable of triggering a biocidal event or has an anti-cancer effect. Suitable labels include radionuclides, photosensitizers, toxin polypeptides, toxic small molecules and other drugs, cytokines (e.g. IL2, IL12, TNF), chemokines, pro-coagulant factors (e.g. tissue factor), enzymes, liposomes, and immune response factors (see, for example, D. Neri (2004) CHIMIA "Tumor Targeting" vol. 58, pages 723-726).

Radionuclides include iodine-131, yttrium-90, indium-111 and technicium-99 and are described in more detail above.

A toxin polypeptide or peptide has cytotoxic or apoptotic activity and may be derived from a microbial, plant, animal or human source. In some embodiments, a toxin polypeptide may be inserted directly into the constant regions of a specific binding member. Examples of toxin polypeptides include *Pseudomonas* exotoxin, ricin α-chain and angiogenin.

Toxic small molecules include chemical compounds with cytotoxic activity, including, for example, DNA-complexing agents or cell cycle inhibitors. In some embodiments, the toxic molecule may be liberated in the vicinity of the target cell by cleavage of a pH- or enzyme-sensitive linker (e.g.

linkers containing imine bonds). Examples of toxic small molecules include maytansine, calicheamicin, epothilone and tubulysin and derivatives thereof.

Immune response factors may include specific binding members which bind to immune effector cells. The binding of the specific binding member may invoke a cell-mediated immune response against the target cell.

In preferred embodiments, a specific binding member of the invention is conjugated with a cytokine. A fusion protein comprising the specific binding member or a polypeptide component thereof (e.g. a heavy chain or a light chain of an antibody or multi-chain antibody fragment, such as a Fab) and the cytokine may be produced. Thus, for example, a VH domain or VL domain of a specific binding member of the invention may be fused to the cytokine. Typically the specific binding member, or component thereof, and cytokine are joined via a peptide linker, e.g. a peptide of about 5-25 residues, e.g. 10-20 residues, preferably about 15 residues. Suitable examples of peptide linkers are given herein. Preferably the cytokine is IL2, more preferably human IL2. The cytokine may be fused upstream (N-terminal) or downstream (C-terminal) of the specific binding member or polypeptide component thereof. A preferred embodiment is a fusion protein comprising specific binding member (especially an antibody molecule, e.g. scFv molecule) of the invention and IL2. Amino acid sequences of such fusion proteins, and nucleic acids comprising nucleotide sequences encoding them, form part of the invention.

Specific binding members of the present invention may be useful in methods of diagnosis, such as tumour imaging, or in the treatment in human or animal subjects, for example for cancer conditions.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

A specific binding member for use in a method of treatment is preferably conjugated with or linked to a functional label which elicits an anti-tumour effect. In preferred embodiments, as noted above, the specific binding member is conjugated with or linked to a cytokine e.g. IL2.

Clinical indications in which a specific binding member as described herein may be used to provide therapeutic benefit include proliferative disorders such as pre-malignant and malignant neoplasms and tumours, (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukaemias and angiogenic diseases.

A pre-malignant or malignant condition may occur in any cell-type, including but not limited to, lung, colon, breast, ovarian, prostate, liver, pancreas, brain, and skin.

A proliferative disorder suitable for treatment as described herein may be characterized by the presence of cells or tissue in which expression of tenascin-C large isoforms, in particular large isoforms comprising the A1 or C domains, is increased or elevated.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors. Appropriate doses of antibody are well known in the art; see Ledermann J. A. et al. (1991) Int J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg to 100 g for systemic applications, and 10 µg to 1 mg for local applications. Typically, the antibody will be a whole antibody, preferably the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine, or anti-emetics.

A further aspect of the invention provides a method of detecting and/or imaging tumour cells comprising administering an antibody as described herein to an individual and detecting the binding of said antibody to tumour cells in said individual.

Preferred antibodies for use in such methods may be conjugated or linked to a detectable label such as a radionuclide or flurophor.

A method of the invention may comprise causing or allowing binding of a specific binding member as provided herein to tenascin-C. As noted, such binding may take place in vivo, e.g. following administration of a specific binding member, or nucleic acid encoding a specific binding member.

The amount of binding of specific binding member to tenascin-C may be determined. In some embodiments, the binding of the specific binding member to a sample obtained from an individual may be determined. In other embodiments, binding of the specific binding member to an antigen may be determined in in vivo, for example in imaging or detecting tumours in the body of an individual.

Quantitation may be related to the amount of the antigen, which may be of diagnostic interest.

The binding of antibodies may be determined by any appropriate means. For example, the antibody may be linked or conjugated to a reporter molecule or detectable label and the presence, amount or localization of the label or reporter on the sample determined.

Binding of an antibody in vivo, for example in a method of molecular imaging, may be determined by radioactive detection (e.g. PET, SPECT), near infrared fluorescence imaging (e.g. diffuse optical tomography, endoscopy), ultrasound (e.g. with targeted microbubble derivatives) and MRI (with targeted magnetic particles).

In other embodiments, binding of the antibody may take place in vitro, for example in ELISA, Western blotting, immunocytochemistry, immuno-precipitation or affinity chromatography.

A method of detecting and/or imaging tumour cells may thus comprise contacting an antibody as described herein with a sample obtained from an individual and detecting the binding of said antibody to tumour cells in said sample.

Preferred antibodies for use in such in vitro methods may be conjugated or linked to a reporter molecule. The reporter molecule may be a radionuclide, fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. For in vivo imaging, radionuclides or flurophors are preferred.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyze reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

The present invention further extends to a specific binding member which competes for binding to tenascin-C with any specific binding member which both binds tenascin-C and comprises a V domain including a CDR with amino acid substantially as set out herein or a V domain with amino acid sequence substantially as set out herein (e.g. a specific binding member as set out herein). Competition between binding members may be assayed easily in vitro, for example by tagging a specific reporter molecule to one binding member which can be detected in the presence of other untagged binding member(s), to enable identification of specific binding members which bind the same epitope or an overlapping epitope. Competition may be determined using standard techniques such as ELISA.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence. Specific binding members according to the present invention may be such that their binding for antigen is inhibited by a peptide with or including the sequence given. In testing for this, a peptide with either sequence plus one or more amino acids may be used. Suitable peptides may be obtained from sequences of the D, C and/or A1 domains of tenascin-C.

Specific binding members which bind a specific peptide may be isolated for example from a phage display library by panning with the peptide(s).

The present invention further provides an isolated nucleic acid encoding a specific binding member of the present invention. Nucleic acid includes DNA and RNA. In a preferred aspect, the invention provides a nucleic acid which codes for a CDR or VH or VL domain of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR, VH or VL domain, or specific binding member as provided itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology,* Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Other methods of the invention comprise conjugating or linking a specific binding member as described herein with a detectable label or anti-cancer agent.

Suitable labels and agents are described above. Labels and agents may be conjugated with a specific binding member using standard chemical means.

Aspects and embodiments of the present invention will now be illustrated by way of example with reference to the following experimentation.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described above and tables described below.

FIG. 1—Schematic representation of the small (A) and large (B) tenascin-C isoform. Several fibronectin type III like domains are subject to alternative splicing, either being included (B) or omitted (A) in the molecule.

EXAMPLE 1

Figure 1:
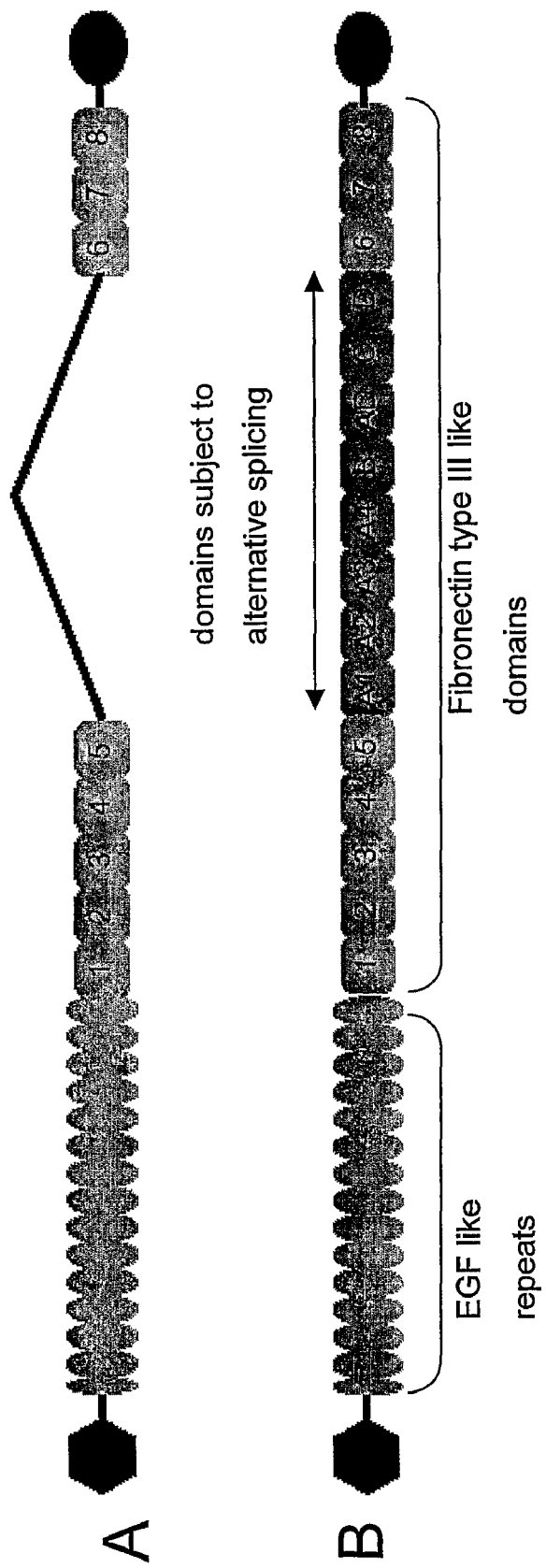
Figure 2:
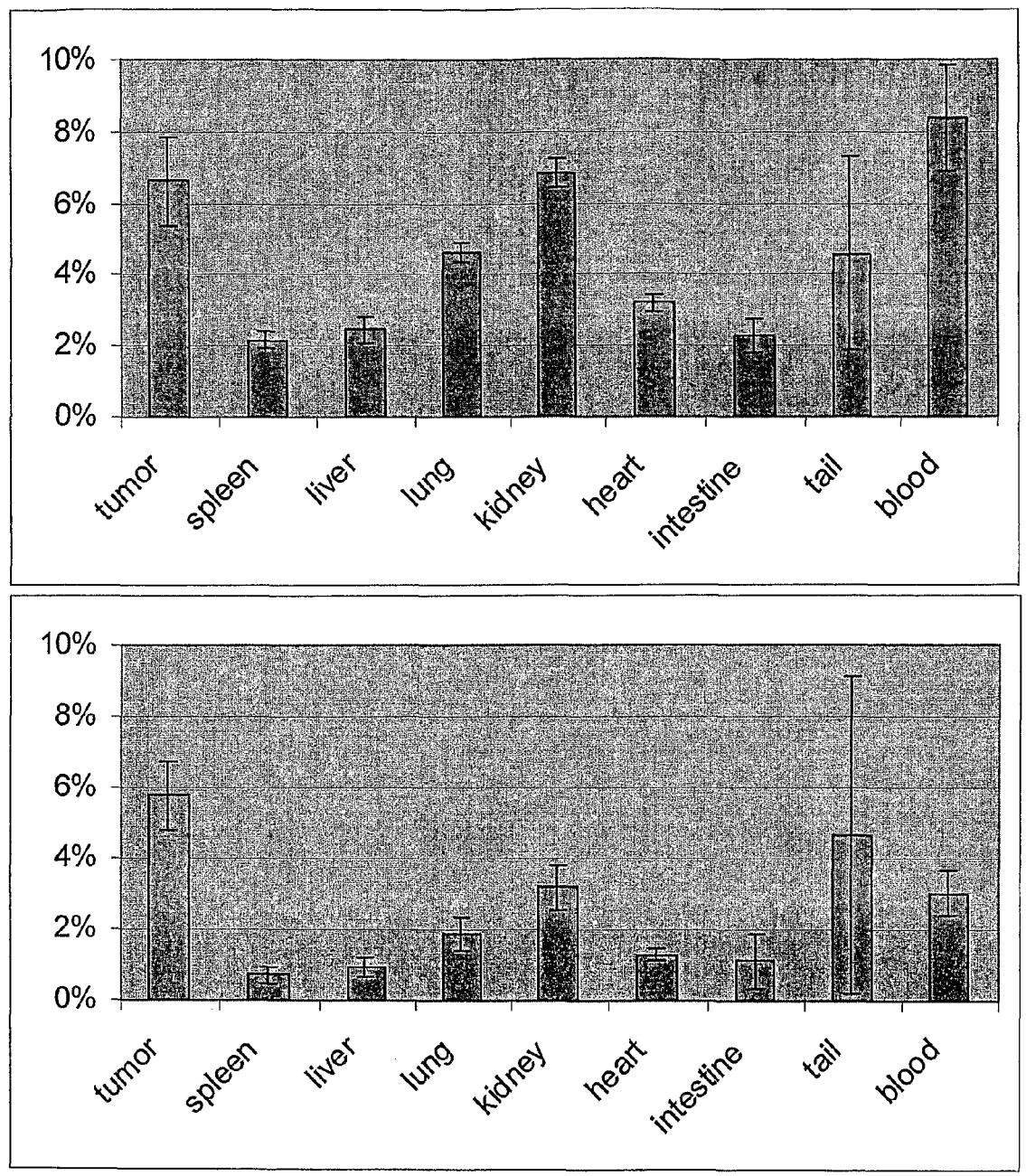
FIG. 2 shows the biodistribution of 4A1-F16-SIP antibody in U87 tumor xenograft bearing nude mice. (A) Values represent the average percent injected dose per gram of tissue within a group of three mice, three (upper) and six (lower) hours after injection. Error bars represent standard deviation.
Figure 3:
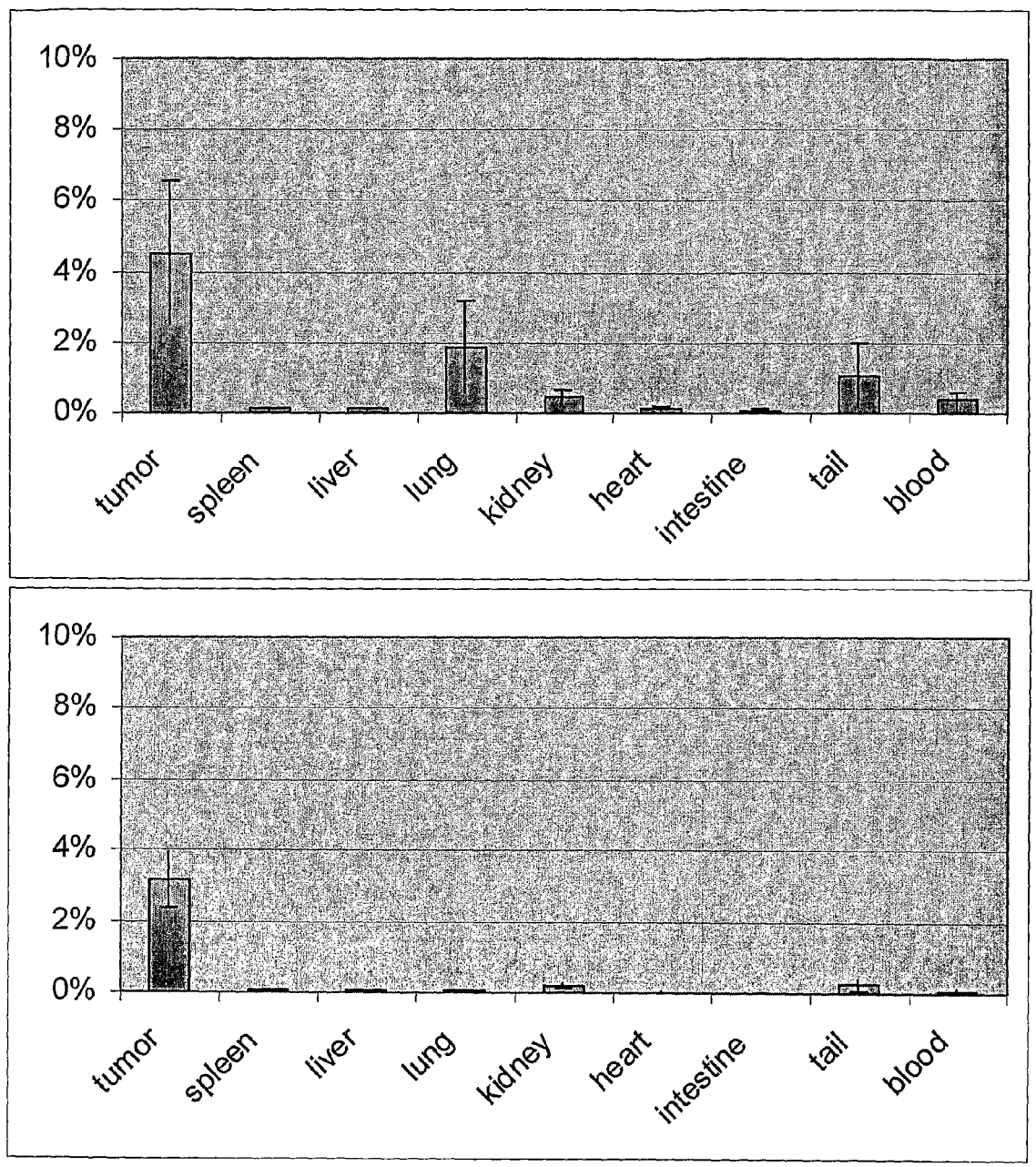
FIG. 3 shows the biodistribution of 4A1-F16-SIP antibody in U87 tumor xenograft bearing nude mice. (A) Values represent the average percent-injected dose per gram of tissue within a group of three mice, 24 (upper) and 48 hours (lower) hours after injection. Error bars represent standard deviation.
Figure 4:
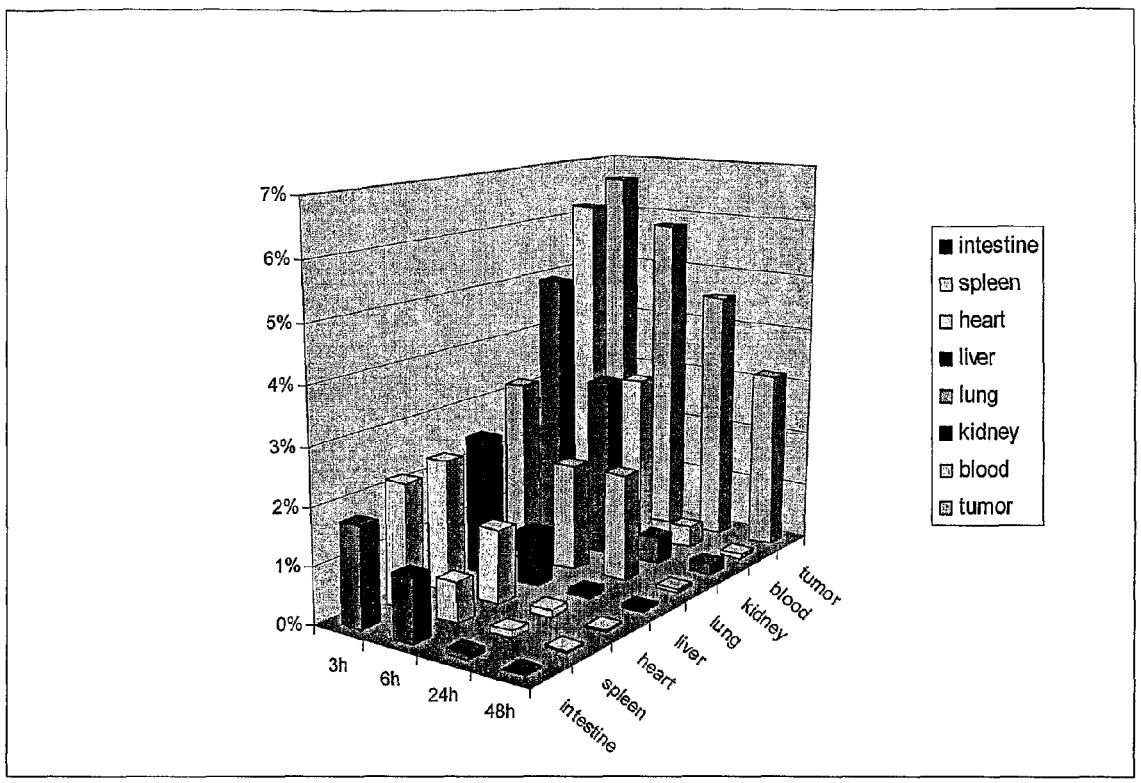
FIG. 4 shows an alternative presentation of the biodistribution data shown in FIGS. 2 and 3.

The gene encoding domain A1 of human tenascin-C was cloned by RT-PCR from mRNA isolated from normal human dermal fibroblasts (NHDF) cultured at pH 7.5 in the absence of serum using PCR oligos TnC-A1 BamHI ba (cgggatcctc-cactgaacaagcccctgag; SEQ ID NO: 84) and TnC-A1 BglII for (ggagatctttcccctgtggaggcctcagc; SEQ ID NO: 85) [16]. The gene was then cloned into pQE12 bacterial expression vector (Qiagen) and expressed in *E. coli* TG-1. Purification was performed by means of the His-tag using Ni-NTA sepharose resin loaded with Nickel (Qiagen).

The purified domain A1 was biotinylated prior to selections, using sulfo-NHS-SS-biotin (Pierce). Biopanning was performed as described in (Viti F, et al *Methods Enzymol* 2000; 326:480-505). Briefly, biotinylated protein (final concentration $10^{-7}$M) was incubated with 600 µl preblocked ETH-2 library phage for 30 minutes. Bound phages were captured by addition of $5.3 \times 10^7$ streptavidin-coated magnetic beads (Dynal). After extensive washing, selected phage was eluted by reducing the disulphide bond in the biotin linker. Isolated phage was amplified in TG-1 and concentrated from the supernatant by polyethylene glycol precipitation. After three rounds of panning, 144 isolated antibody clones were screened by ELISA performed as described in Viti F, et al *Methods Enzymol* 2000; 326:480-505. Streptavidin-coated ELISA plates (StreptaWell High Bind, Roche) were incubated with biotinylated antigen, supernatant of induced monoclonal *E. coli* TG-1 cultures expressing scFv antibody fragments were added and bound antibody were detected with the M2 monoclonal antibody, followed by anti-mouse Immunoglobulin G-HRP conjugate. The antibody clones with the highest signal were analyzed by real-time interaction analysis using a BIAcore 3000 instrument. The three best clones were purified on a protein A-sepharose column and tested by immunohistochemistry on various tumor cryosections.

One of the clones which exhibited a selective staining pattern in immunohistochemistry, scFv (3A1-D5), was chosen for affinity maturation. An affinity maturation library was constructed in a phagemid vector, pDN322 (Pini A et al. *J Biol Chem* 1998; 273:21769-21776), by inserting random mutations at positions 31-33 within the complementarity-determining region 1 of the variable heavy chain (VH CDR1) using PCR oligonucleotides LMB3 long ba (caggaaacagctatgaccat-gattac; SEQ ID NO: 86, priming upsteam of the 5' end of the antibody gene) and DP47CDR1mut for (agcctggcggac-ccagctcgcmnnmnnmnngctaaaggtgaatccagaggctgc; SEQ ID NO: 87). The 3' end of the antibody gene was amplified using primers DP47CDR1 ba (gagctgggtccgccaggctcc; SEQ ID NO: 88) and fdseq long for (gacgttagtaaatgaattttctgtatgagg; SEQ ID NO: 89). The two fragments were assembled by PCR using primers LMB3 long ba and fdseq long for.

Biopanning of the affinity maturation library was performed with biotinylated antigen. After two rounds of panning (as described above, but using $10^{-8}$ M biotinylated antigen), a total of 382 antibody clones were screened by ELISA. 69 clones which were positive in ELISA were further characterized by M2-ELISA (Scheuermann J et al *J Immunol Methods* 2003; 276:129-134) to evaluate $k_{off}$ values of the individual antibody clones. Briefly, supernatant containing scFv antibodies were added onto a surface coated with anti-Flag M2 monoclonal antibody (SIGMA). After addition of biotinylated antigen and incubation to the equilibrium, an excess of unbiotinylated antigen was added as competitor. After competition times of 0, 30, 60, 90 and 120 minutes, respectively, the remaining fraction of biotinylated antigen was detected using Streptavidin-HRP conjugate.

BIAcore was used to rank different ELISA-positive clones based on their dissociation profile. The five best clones were chosen for purification on an antigen-coated sepharose column. Purified antibodies were subject to size exclusion chromatography and resulting monomeric scFv antibody fragment fractions were used to determine affinity constants and kinetic parameters using BIAcore 3000.

The antibody with the best dissociation constant ($K_D$), 4A1-F16, was cloned into a bivalent minibody format, by genetically fusing the scFv(4A1-F16) sequence in front of the 5'-end of the gene encoding the CH4 domain of human immunoglobulin E, yielding a small immune protein (SIP) (Borsi L et al *Int J Cancer* 2002; 102:75-85), termed 4A1-F16-SIP. The CH4 domain promotes homodimerization, increasing functional affinity of the antibody due to the higher avidity.

Immunohistochemistry was performed with the anti-A1 domain of tenascin-C antibody fragment scFv(3A1-D5) on human head-and-neck cancer tissues. Primary antibody was detected by means of the peptidic FLAG-tag with was appended to the C-terminus of the scFv antibody, using the monoclonal anti-FLAG antibody M2 (SIGMA) followed by the APAAP system (DAKO). scFv(3A1-D5) and scFv(4A1-F16) were observed to strongly stain the tumor stroma and neovascular structures on cryosections of various head-and-neck cancers, whereas they did not react with normal mouth mucosa of a healthy donor.

The tumor targeting ability of 4A1-F16-SIP was assessed as follows:

Tumors were induced in Balb/C nu/nu mice by subcutaneous injection of $3 \times 10^6$ U87 human glioblastoma cells per mouse (ATCC). 20 to 25 days post injection, when tumors reached a size of 300-1500 mm³, radiolabeled antibody was injected.

The preparation of the antibody included further purification of affinity-purified 4A1-F16-SIP antibody by size exclusion chromatography on superdex 75. The fraction representing the homodimeric form (75 kDa) was collected and subsequently labeled with iodine-125 (Amersham) using iodogen (Pierce).

Approximately 5 µg of antibody were injected intravenously into the tail vein of tumor bearing mice. After 3, 6, 24 and 48 hours, respectively, three mice were sacrificed, the organs excised and accumulation of I-125 determined in a γ-counter.

EXAMPLE 2

The gene encoding domain C of human tenascin-C was cloned into vector pQE12 (Qiagen) [Carnemolla B et al. Am J Pathol 1999; 154:1345-1352, Balza E et al. FEBS Lett 1993; 332:39-43], and expressed in *E. coli* TG-1. Purification was performed by means of the His-tag using Ni-NTA sepharose resin loaded with Nickel (Qiagen).

The purified domain C was biotinylated prior to selections, using sulfo-NHS-SS-biotin (Pierce). Biopanning was performed like described in [Viti F, et al Methods Enzymol 2000; 326:480-505], but using an alternate panning procedure on streptavidin- and avidin-coated plates. Briefly, biotinylated protein (final concentartion $10^{-7}$ M) was incubated with 600 µl preblocked ETH-2 library phage for 30 minutes. Bound phage were captured on plastic microtitre plates coated with avidin ($1^{st}$ and $3^{rd}$ round of panning) or streptavidin ($2^{nd}$ round of panning). After extensive washing, selected phage was eluted by reducing the disulphide bond in the biotin linker. Isolated phage was amplified in TG-1 and concentrated from the supernatant by polyethylene glycol precipitation. After three rounds of panning, several dozens antibody clones were screened by ELISA performed as described in [Viti F. et al Methods Enzymol 2000; 326:480-505].

Streptavidin-coated ELISA plates (StreptaWell High Bind, Roche) were incubated with biotinylated antigen, supernatant of induced monoclonal *E. coli* TG-1 cultures expressing scFv antibody fragments were added and bound antibody were detected with an anti-peptide tag antibody, followed by anti-mouse Immunoglobulin G-HRP conjugate. The antibody clones with the highest signal were analyzed by real-time interaction analysis using a BIAcore 3000 instrument. The three best clones were purified on a protein A-sepharose column and tested by immunohistochemistry on various tumor cryosections. One of the clones which exhibited a selective staining pattern in immunohistochemistry, scFv (A12), was chosen for affinity maturation. An affinity maturation library was constructed in phagemid vector pHEN1 [Hoogenboom H R et al. Nucleic Acids Res 1991; 19:4133-4137], by inserting random mutations at positions 31-33 within VH CDR1 and at positions 52,52a,53 and 56 within VH CDR2, using PCR oligonucleotides LMB3 long ba (caggaaacagctatgaccatgattac SEQ ID NO: 86, priming upsteam of the 5' end of the antibody gene), DP47CDR1 for (ctggagcctggcggacccagctcatmnnmnnmnngctaaaggtgaatccagaggctgc; SEQ ID NO: 90), DP47CDR1 ba (tgggtccgccaggctccag; SEQ ID NO: 91), DP47CDR2 for (gcccttcacggagtctgcgtagtatgtmnnaccaccmnnmnnmnnaatagctgagacccac Tcc; SEQ ID NO: 92), DP47CDR2 ba (acatactacgcagactccgtgaagggc; SEQ ID NO: 93) and fdseq long for (gacgttagtaaatgaattttctgtatgagg; SEQ ID NO: 89).

Biopanning of the affinity maturation library was performed with biotinylated antigen. After two rounds of panning (as described above), a total of 382 antibody clones were screened by ELISA clones which were positive in ELISA were further characterized by BIAcore to rank different ELISA-positive clones based on their dissociation profile. Among the clones tested, scFv(E10) showed the most promising performance.

Immunohistochemistry was performed with the anti-C domain of tenascin-C antibody fragment scFv(A12) on human glioblastoma multiform tissue. Primary antibody was detected by means of the peptidic myc-tag which was appended to the C-terminus of the scFv antibody, using monoclonal anti-myc tag antibody E10, followed by the APAAP system (DAKO). These antibodies were observed to react specifically with perivascular structures, as depicted by immunohistochemistry on glioblastoma cyrosections.

EXAMPLE 3

Using a protocol similar to that described in Example 2, further scFv against the C domain of tenascin-C were isolated, and designated F4 and G11, respectively. F4 and G11 have VL domains differing by two amino acids, and have the same VH domain. The VH and VL domains were joined through a peptide linker having the amino acid sequence set out in SEQ ID NO: 37 or SEQ ID NO: 39, as encoded by SEQ ID NO: 36 or SEQ ID NO: 38, respectively.

EXAMPLE 4

The gene encoding human domain D of tenascin C (TnC-D) was cloned by RT-PCR from total RNA isolated from the human melanoma cell line SKMel-28 using PCR oligos TnC-D BamHI ba (cgggatccgttacagaagccgaaccggaa—SEQ ID NO: 72) and TnC-D BglII for (cgggatccgttacagaagccgaac-cggaa—SEQ ID NO: 73) [16]. The amplified fragment was subcloned into the bacterial expression vector pQE12 which introduced a His-tag at the C-terminus of the protein. The gene encoding the mouse isoform of TnC-A1 was isolated by PCR from an expressed sequence tag (EST) clone deriving from infiltrating ductal carcinoma tissue, using the primers
mmTnC-A1 EcoBa
(agaattcattaaagaggagaaattaac-
tatgagaggatcctccacggaagaagtgccttc—SEQ ID NO: 74) and mmTnC-A1 BglFo
(tgagatcttgtccctgtggaggtctcggc—SEQ ID NO: 75), and cloned into vector pQE12 (Qiagen).

The ETH-2 library [26] was panned with 100 nM biotinylated coated human TnC-D, and bound phage was captured with streptavidin-coated magnetic beads. After three rounds of panning, supernatants obtained from 188 individual clones were screened by ELISA on biotinylated human TnC-D and on biotinylated mouse TnC-D. Most of the clones which recognized the human isoform also reacted with the mouse isoform of TnC-D.

Supernatants of ELISA positive clones were tested in a second ELISA and screened by BIAcore. The six best were clones extensively characterized, and scFv(F4) was identified to be the best clones. scFv(F4) bound to both human and mouse TnC-D with the same affinity.

scFv(F4) exclusively recognized proteins that contained domain D in ELISA, and did not react with proteins which were structurally related to domain D. However, it only reacted very weakly with tumour structures in immunohistochemistry, leading to signals which were difficult to discriminate from background. This is presumably due to the low affinity of scFv(F4).

ScFv(F4) was used as template for affinity maturation by CDR loop mutagenesis [26]. The residues chosen for randomization were $V_L$ CDR1 positions 30, 31, 32 and $V_H$ CDR2 positions 50, 52 and 53 (numbering according to Kabat; [30]. The library was cloned into phagemid vector pHEN which appended a myc tag to the C-terminus of the $V_L$ [31].

The first round of panning with affinity maturation library phage was performed with biotinylated human TnC-D, the second round with biotinylated mouse TnC-D. 750 clones were screened by ELISA on biotinylated human TnC-D, approximately 5% were positive. After further characterization of the antibodies by BIAcore and ELISA, scFv(D11) was identified as best clone. ScFv (D11). Affinity measurements with monomeric fractions by BIAcore showed that scFv (D11) had a two- to four-fold improved affinity compared to the parental clone scFv(F4). The mouse isoform was bound with slightly higher affinity than the human isoform.

scFv(D11) gave good results in immunohistochemistry on different tumour tissues. Human oral squamous cell carcinoma, human bladder carcinoma, A375 human melanoma grown in nude mice, and F9 murine F9 teratocarcinoma grown in SvEv 129 mice were all stained with scFv(D11). The antibody reacted strongly with the stroma of human tumours like head and neck cancer or bladder carcinoma, as well as on various human and murine tumour models.

Next we randomized residues within the CDR1 and CDR1 of $V_H$ of scFv(D11). We chose residues 31, 32, 33 in the $V_H$ CDR1 and residues 52, 52a, 53 and 56 in the $V_H$ CDR2 for randomisation (Kabat numbering; [32]). Two rounds of selection by phage display were performed, using $10^{-8}$ M human TnC-D as antigen. To increase the stringency of the selections, 10 nM purified soluble scFv(D11) was mixed with the phage prior to addition of the antigen in the first round, and a 1000-fold excess of non-biotinylated antigen was added to the pre-incubated antigen-phage mixture in the second round of panning.

Figure 5:
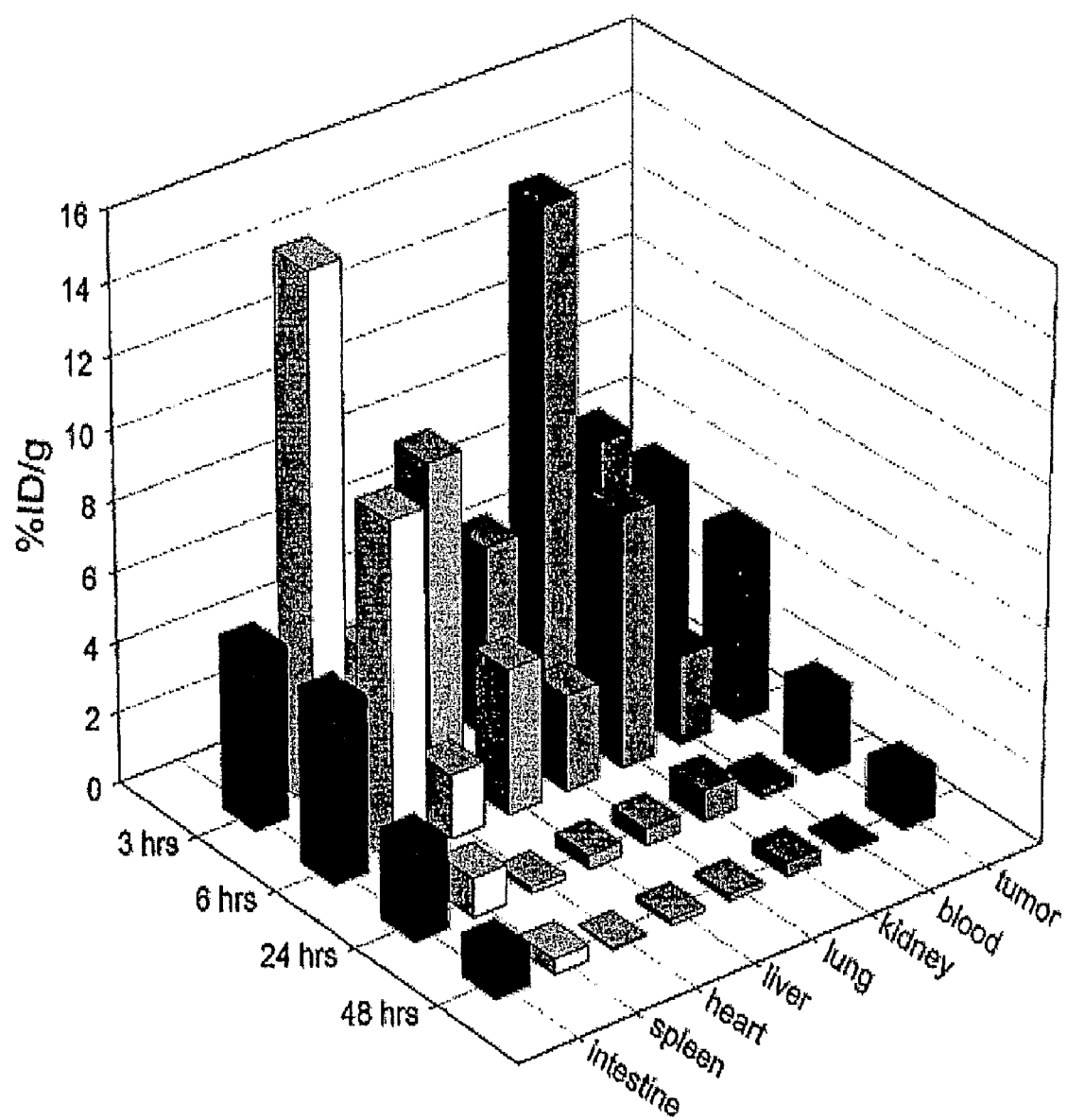
FIG. 5 shows biodistribution of SIP(P12). 3.5 µg SIP(P12) were injected into mice bearing a subcutaneous U87 human glioblastoma tumour. Each time point is represented by four animals.

25% of the 384 clones screened after two rounds were positive on human biotinylated TnC-D in ELISA. After further characterization, it was scFv(P12) which was identified as best clone. Its affinity on human TnC-D was improved by factor 4.8, compared to scFv(D11).

scFv(P12) was cloned into SIP (small immunoprotein) format [25]. The in vivo targeting performance of SIP (P12) was evaluated by biodistribution experiments in U87 human glioblastoma xenograft bearing nude mice. $^{125}$I-labeled SIP antibodies were injected i.v. and 3, 6, 24 and 48 hr later, animals were sacrificed, the organs excised, weighed and radioactivity was counted. SIP(P12) was cleared within 24 hours after injection from most organs, and a specific accumulation at the tumor site was observed after 24 and 48 hours, with tumour-to-blood ratios of up to 15 (FIG. 5 and Table 1).

TABLE

| Biodistribution of radiolabelled P12-SIP in U87 tumor-bearing nude mice | | | | |
|---|---|---|---|---|
| | 3 h | 6 h | 24 h | 48 h |
| tumor | 5.60 ± 0.84 | 5.17 ± 1.06 | 2.27 ± 0.53 | 1.49 ± 0.45 |
| intestine | 4.93 ± 0.99 | 5.02 ± 1.37 | 2.57 ± 0.74 | 1.19 ± 0.38 |
| spleen | 14.96 ± 4.49 | 9.58 ± 1.23 | 1.10 ± 0.26 | 0.44 ± 0.21 |
| heart | 3.72 ± 0.18 | 1.79 ± 0.12 | 0.17 ± 0.04 | 0.05 ± 0.01 |
| liver | 8.49 ± 0.76 | 4.10 ± 0.41 | 0.39 ± 0.09 | 0.15 ± 0.05 |
| lung | 5.45 ± 0.29 | 2.70 ± 0.53 | 0.46 ± 0.05 | 0.16 ± 0.05 |
| kidney | 14.32 ± 0.62 | 7.20 ± 0.42 | 0.89 ± 0.19 | 0.39 ± 0.16 |
| blood | 7.21 ± 0.53 | 2.54 ± 0.44 | 0.29 ± 0.07 | 0.10 ± 0.05 |
| tumor size (mg) | 99.5 ± 62.0 | 53.5 ± 18.2 | 102.3 ± 89.6 | 48.8 ± 35.2 |

Results are expressed as percent injected antibody dose per gram of tissue (% ID/g) ± SD

REFERENCES

1. Bosslet K et al. *Cancer Res* 1998; 58:1195-1201
2. Jain R K. *Adv Drug Deliv Rev* 2001; 46:149-168
3. Kohler G, Milstein C *Nature* 1975; 256:495-497
4. Winter G et al *Annu Rev Immunol* 1994; 12:433-455
5. Halin C et al. *Cancer Res* 2003; 63:3202-3210
6. Halin C et al. *Nat Biotechnol* 2002; 20:264-269
7. Nilsson F et al *Cancer Res* 2001; 61:711-716
8. Borsi L et al. *Blood* 2003; 102:4384-4392
9. Carnemolla B et al. *Blood* 2002; 99:1659-1665
10. Zardi L et al. *Embo J* 1987; 6:2337-2342
11. Castellani P et al. *Am J Pathol* 2002; 161:1695-1700
12. Castellani P et al *Int J Cancer* 1994; 59:612-618
13. Carnemolla B et al. *Int J Cancer* 1996; 68:397-405
14. Borsi L et al *Int J Cancer* 1992; 52:688-692
15. Carnemolla B et al. *Eur J Biochem* 1992; 205:561-567

16. Borsi L et al *J Biol Chem* 1995; 270:6243-6245
17. Riva P et al. *Int J Cancer* 1992; 51:7-13
18. Riva P et al. *Cancer Res* 1995; 55:5952s-5956s
19. Paganelli G et al *Eur J Nucl Med* 1994; 21:314-321
20. Reardon D A et al. *J Clin Oncol* 2002; 20:1389-1397
21. Bigner D D et al. *J Clin Oncol* 1998; 16:2202-2212
22. Carnemolla B et al. *Am J Pathol* 1999; 154:1345-1352
23. Katenkamp K et al. *J Pathol* 2004; 203:771-779
24. Viti F, et al *Methods Enzymol* 2000; 326:480-505
25. Borsi L et al. *Int J Cancer* 2002; 102:75-85
26. Pini A et al. *J Biol Chem* 1998; 273:21769-21776
27. Scheuermann J et al *J Immunol Methods* 2003; 276:129-134
28. Balza E et al. *FEBS Lett* 1993; 332:39-43
29. Hoogenboom H R et al. *Nucleic Acids Res* 1991; 19:4133-4137
30. Ignatovich, O., et al. (1997). *J Mol Biol* 268(1): 69-77.31.
31. Hoogenboom & Winter (1992). *J Mol Biol* 227(2): 381-8.
32. Tomlinson, et al. (1992). *J Mol Biol* 227(3): 776-98.

The invention claimed is:

1. A specific binding member which binds human tenascin-C and comprises:
   i) a D5 VH domain of SEQ ID NO: 12 and VL domain of SEQ ID NO: 50;
   ii) a 4A1-F16 VH domain of SEQ ID NO: 2 and VL domain of SEQ ID NO: 50; or
   iii) an antibody-VH domain comprising VH CDRs 1, 2, and 3 wherein:
      VH CDR1 is SEQ ID NO: 5 or SEQ ID NO: 13;
      VH CDR2 is SEQ ID NO: 6; and
      VH CDR3 is SEQ ID NO: 7;
   and, VL domain comprising VL CDRs 1, 2, and 3 wherein:
      VL CDR1 is SEQ ID NO. 8;
      VL CDR2 is SEQ ID NO. 9; and,
      VL CDR3 is SEQ ID NO. 10.

2. A specific binding member according to claim 1, that comprises an scFv antibody molecule.

3. A specific binding member according to claim 1 that comprises an antibody constant region.

4. A specific binding member according to claim 1 that comprises a whole antibody.

5. A specific binding member according to claim 1, conjugated to a detectable label or to a cytokine.

6. A specific binding member according to claim 5 wherein a VH domain or VL domain of the specific binding member is conjugated to a cytokine via a peptide linker as a fusion protein.

7. A specific binding member according to claim 5 wherein the cytokine is IL2.

8. A specific binding member according to claim 1 conjugated to a cytotoxic agent.

9. A specific binding member according to claim 1 conjugated to a detectable label selected from the group consisting of a radionuclide or a fluorophore.

10. A specific binding member according to claim 9, wherein said detectable label is iodine-131.

11. A specific binding member according to any one of claims 1 to 3, 5 to 10, comprising a small immune protein (SIP), wherein the SIP comprises an scFv molecule comprising the VH domain sequence of SEQ ID NO: 2 and the VL domain sequence of SEQ ID NO: 50, fused to the CH4 domain of human immunoglobulin E, said SIP optionally being homodimeric.

12. An isolated specific binding member that binds human tenascin-C, comprising
   an antibody VH domain with amino acid sequence SEQ ID NO: 2 or an amino acid sequence having 1 or 2 amino acid sequence alterations in SEQ ID NO: 2 and
   an antibody VL domain with amino acid sequence SEQ ID NO: 50 or an amino acid sequence having 1 or 2 amino acid sequence alterations in SEQ ID NO: 50.

13. A specific binding member according to claim 12, comprising a small immune protein (SIP), wherein the SIP comprises an scFv molecule comprising the VH domain sequence of SEQ ID NO: 2 and the VL domain sequence of SEQ ID NO: 50, fused to the CH4 domain of human immunoglobulin E, said SIP optionally being homodimeric.

14. A specific binding member according to claim 12 wherein the specific binding member is conjugated to iodine-131.

* * * * *

SEQUENCE LISTING

```
<160> NUMBER OF SEQ ID NOS: 93

<210> SEQ ID NO 1
<211> LENGTH: 348
<212> TYPE: DNA
<213> ORGANISM: Homo sapiens
<220> FEATURE:
<223> OTHER INFORMATION: 4A1-F16 VH domain nucleotide sequence

<400> SEQUENCE: 1
gaggtgcagc tgttggagtc tgggggaggc ttggtacagc ctgggggtc cctgagactc      60 tcctgtgcag cctctggatt cacctttagc cggtatggtg cgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagcgcat     300
aatgcttttg actactgggg ccagggaacc ctggtcaccg tgtcgaga                  348

<210> SEQ ID NO 2
<211> LENGTH: 116
<212> TYPE: PRT
<213> ORGANISM: Homo sapiens
<220> FEATURE:
<223> OTHER INFORMATION: 4A1-F16 VH domain amino acid sequence

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Ala Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 3
<211> LENGTH: 327
<212> TYPE: DNA
<213> ORGANISM: Homo sapiens
<220> FEATURE:
<223> OTHER INFORMATION: 4A1-F16 & 3A1-D5 VL domain nucleotide sequence
```

<400> SEQUENCE: 3

```
tcgtctgagc tgactcagga ccctgctgtg tctgtggcct tgggacagac agtcaggatc    60
acatgccaag agacagcct cagaagctat tatgcaagct ggtaccagca gaagccagga   120
```

```
tcgtctgagc tgactcagga ccctgctgtg tctgtggcct tgggacagac agtcaggatc    60
acatgccaag agacagcct  cagaagctat tatgcaagct ggtaccagca gaagccagga   120
caggcccctg tacttgtcat ctatggtaaa acaaccggc cctcagggat cccagaccga   180
ttctctggct ccagctcagg aaacacagct tccttgacca tcactgggc tcaggcggaa   240 gatgaggctg actattactg taactcctct gtttatacta tgccgcccgt ggtattcggc   300
ggagggacca agctgaccgt cctaggc                                      327
```

<210> SEQ ID NO 4
<211> LENGTH: 109
<212> TYPE: PRT
<213> ORGANISM: Homo sapiens
<220> FEATURE:
<223> OTHER INFORMATION: 4A1-F16 & 3A1-D5 VL domain amino acid sequence

<400> SEQUENCE: 4

```
Ser Ser Glu Leu Thr Gln Asp Pro Ala Val Ser Val Ala Leu Gly Gln
  1               5                  10                  15
Thr Val Arg Ile Thr Cys Gln Gly Asp Ser Leu Arg Ser Tyr Tyr Ala
             20                  25                  30
Ser Trp Tyr Gln Gln Lys Pro Gly Gln Ala Pro Val Leu Val Ile Tyr
         35                  40                  45
Gly Lys Asn Asn Arg Pro Ser Gly Ile Pro Asp Arg Phe Ser Gly Ser
     50                  55                  60
Ser Ser Gly Asn Thr Ala Ser Leu Thr Ile Thr Gly Ala Gln Ala Glu
 65                  70                  75                  80
Asp Glu Ala Asp Tyr Tyr Cys Asn Ser Ser Val Tyr Thr Met Pro Pro
                 85                  90                  95
Val Val Phe Gly Gly Gly Thr Lys Leu Thr Val Leu Gly
            100                 105
```

<210> SEQ ID NO 5
<211> LENGTH: 5
<212> TYPE: PRT
<213> ORGANISM: Homo sapiens
<220> FEATURE:
<223> OTHER INFORMATION: 4A1-F16 VH CDR1 amino acid sequence

<400> SEQUENCE: 5

```
Arg Tyr Gly Ala Ser
  1               5
```

<210> SEQ ID NO 6
<211> LENGTH: 17
<212> TYPE: PRT
<213> ORGANISM: Homo sapiens
<220> FEATURE:
<223> OTHER INFORMATION: 4A1-F16 & 3A1-D5 VH CDR2 amino acid sequence

<400> SEQUENCE: 6

```
Ala Ile Ser Gly Ser Gly Gly Ser Thr Tyr Tyr Ala Asp Ser Val Lys
  1               5                  10                  15
Gly
```

<210> SEQ ID NO 7
<211> LENGTH: 7
<212> TYPE: PRT
<213> ORGANISM: Homo sapiens
<220> FEATURE:

<223> OTHER INFORMATION: 4A1-F16 & 3A1-D5 VH CDR3 amino acid sequence

<400> SEQUENCE: 7

Ala His Asn Ala Phe Asp Tyr
1               5

<210> SEQ ID NO 8
<211> LENGTH: 11
<212> TYPE: PRT
<213> ORGANISM: Homo sapiens
<220> FEATURE:
<223> OTHER INFORMATION: 4A1-F16 & 3A1-D5 VL CDR1 amino acid sequence

<400> SEQUENCE: 8

Gln Gly Asp Ser Leu Arg Ser Tyr Tyr Ala Ser
1               5                   10

<210> SEQ ID NO 9
<211> LENGTH: 7
<212> TYPE: PRT
<213> ORGANISM: Homo sapiens
<220> FEATURE:
<223> OTHER INFORMATION: 4A1-F16 & 3A1-D5 VL CDR2 amino acid sequence

<400> SEQUENCE: 9

Gly Lys Asn Asn Arg Pro Ser
1               5

<210> SEQ ID NO 10
<211> LENGTH: 11
<212> TYPE: PRT
<213> ORGANISM: Homo sapiens
<220> FEATURE:
<223> OTHER INFORMATION: 4A1-F16 & 3A1-D5 VL CDR3 amino acid sequence

<400> SEQUENCE: 10

Asn Ser Ser Val Tyr Thr Met Pro Pro Val Val
1               5                   10

<210> SEQ ID NO 11
<211> LENGTH: 348
<212> TYPE: DNA
<213> ORGANISM: Homo sapiens
<220> FEATURE:
<223> OTHER INFORMATION: 3A1-D5 VH domain nucleotide sequence

<400> SEQUENCE: 11
gaggtgcagc tgttggagtc tgggggaggc ttggtacagc ctgggggtc cctgagactc        60 tcctgtgcag cctctggatt cacctttagc agctatgccg cgagctgggt ccgccaggct      120
ccagggaagg gctggagtg gtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaagcgcat      300
aatgcttttg actactgggg ccagggaacc ctggtcaccg tgtcgaga                  348

<210> SEQ ID NO 12
<211> LENGTH: 116
<212> TYPE: PRT
<213> ORGANISM: Homo sapiens
<220> FEATURE:
<223> OTHER INFORMATION: 3A1-D5 VH domain amino acid sequence

<400> SEQUENCE: 12

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Ala Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 13
<211> LENGTH: 5
<212> TYPE: PRT
<213> ORGANISM: Homo sapiens
<220> FEATURE:
<223> OTHER INFORMATION: 3A1-D5 VH CDR1 amino acid sequence

<400> SEQUENCE: 13

Ser Tyr Ala Ala Ser
1               5

<210> SEQ ID NO 14
<211> LENGTH: 354
<212> TYPE: DNA
<213> ORGANISM: Homo sapiens
<220> FEATURE:
<223> OTHER INFORMATION: E10 VH domain nucleotide sequence

<400> SEQUENCE: 14
gaggtgcagc tggtggagtc tgggggaggc ttggtacagc ctggggggtc cctgagactc      60
tcctgtgcag cctctggatt cacctttagc ggtagtcgta tgggctgggt ccgccaggct     120
ccagggaagg gctggagtg gtctcagct attaatgagg agggtggtca gacatactac       180
gcagactccg tgaagggccg gttcaccatc tccagagaca attccaagaa cacgctgtat     240
ctgcaaatga acagcctgag agccgaggac acggccgtat attactgtgc gaaacatccg     300
ccgcatcggc cgtttgacta ctggggccag ggaaccctgg tcaccgtgtc gaga           354

<210> SEQ ID NO 15
<211> LENGTH: 118
<212> TYPE: PRT
<213> ORGANISM: Homo sapiens
<220> FEATURE:
<223> OTHER INFORMATION: E10 VH domain amino acid sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Arg Met Gly Trp Val Arg Gln Ala Pro Gly Lys Gly Leu Glu Trp Val
        35                  40                  45

Ser Ala Ile Asn Glu Glu Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys His Pro Pro His Arg Pro Phe Asp Tyr Trp Gly Gln Gly Thr
                100                 105                 110

Leu Val Thr Val Ser Arg
        115

<210> SEQ ID NO 16
<211> LENGTH: 327
<212> TYPE: DNA
<213> ORGANISM: Homo sapiens
<220> FEATURE:
<223> OTHER INFORMATION: E10 & A12 VL domain nucleotide sequence

<400> SEQUENCE: 16
tcgtctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa acaaccggc cctcagggat cccagaccga     180
ttctctggct ccagctcagg aaacacagct tccttgacca tcactgggc tcaggcggaa     240 gatgaggctg actattactg taactcctct catgggcccc gtaggcctgt ggtattcggc     300
ggagggacca agctgaccgt cctaggc                                        327

<210> SEQ ID NO 17
<211> LENGTH: 109
<212> TYPE: PRT
<213> ORGANISM: Homo sapiens
<220> FEATURE:
<223> OTHER INFORMATION: E10 & A12 VL domain amino acid sequence

<400> SEQUENCE: 17

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser His Gly Pro Arg Arg Pro
                85                  90                  95

Val Val Phe Gly Gly Gly Thr Lys Leu Thr Val Leu Gly
                100                 105

<210> SEQ ID NO 18
<211> LENGTH: 5
<212> TYPE: PRT
<213> ORGANISM: Homo sapiens
<220> FEATURE:
<223> OTHER INFORMATION: E10, F4 & G11 VH CDR1 amino acid sequence

<400> SEQUENCE: 18

Gly Ser Arg Met Gly
1               5

<210> SEQ ID NO 19
<211> LENGTH: 17
```

```
<212> TYPE: PRT
<213> ORGANISM: Homo sapiens
<220> FEATURE:
<223> OTHER INFORMATION: E10, F4 & G11 VH CDR2 amino acid sequence

<400> SEQUENCE: 19

Ala Ile Asn Glu Glu Gly Gly Gln Thr Tyr Tyr Ala Asp Ser Val Lys
1               5                   10                  15

Gly

<210> SEQ ID NO 20
<211> LENGTH: 9
<212> TYPE: PRT
<213> ORGANISM: Homo sapiens
<220> FEATURE:
<223> OTHER INFORMATION: E10, A12, F4 & G11 VH CDR3 amino acid sequence

<400> SEQUENCE: 20

His Pro Pro His Arg Pro Phe Asp Tyr
1               5

<210> SEQ ID NO 21
<211> LENGTH: 11
<212> TYPE: PRT
<213> ORGANISM: Homo sapiens
<220> FEATURE:
<223> OTHER INFORMATION: E10 & A12 VL CDR1 amino acid sequence

<400> SEQUENCE: 21

Gln Gly Asp Ser Leu Arg Ser Tyr Tyr Ala Ser
1               5                   10

<210> SEQ ID NO 22
<211> LENGTH: 7
<212> TYPE: PRT
<213> ORGANISM: Homo sapiens
<220> FEATURE:
<223> OTHER INFORMATION: E10, A12 & G11 VL CDR2 amino acid sequence

<400> SEQUENCE: 22

Gly Lys Asn Asn Arg Pro Ser
1               5

<210> SEQ ID NO 23
<211> LENGTH: 11
<212> TYPE: PRT
<213> ORGANISM: Homo sapiens
<220> FEATURE:
<223> OTHER INFORMATION: E10 & A12 VL CDR3 amino acid sequence

<400> SEQUENCE: 23

Asn Ser Ser His Gly Pro Arg Arg Pro Val Val
1               5                   10

<210> SEQ ID NO 24
<211> LENGTH: 354
<212> TYPE: DNA
<213> ORGANISM: Homo sapiens
<220> FEATURE:
<223> OTHER INFORMATION: A12 VH domain nucleotide sequence

<400> SEQUENCE: 24
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
```

```
gcagactccg tgaagggccg gttcaccatc tccagagaca attccaagaa cacgctgtat    240
ctgcaaatga acagcctgag agccgaggac acggccgtat attactgtgc gaaacatccg    300
ccgcatcggc cgtttgacta ctggggccag ggaaccctgg tcaccgtgtc gaga          354
```

<210> SEQ ID NO 25
<211> LENGTH: 118
<212> TYPE: PRT
<213> ORGANISM: Homo sapiens
<220> FEATURE:
<223> OTHER INFORMATION: A12 VH domain amino acid sequence

<400> SEQUENCE: 25

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Pro His Arg Pro Phe Asp Tyr Trp Gly Gln Gly Thr
            100                 105                 110

Leu Val Thr Val Ser Arg
        115
```

<210> SEQ ID NO 26
<211> LENGTH: 5
<212> TYPE: PRT
<213> ORGANISM: Homo sapiens
<220> FEATURE:
<223> OTHER INFORMATION: A12 VH CDR1 amino acid sequence

<400> SEQUENCE: 26

```
Ser Tyr Ala Met Ser
1               5
```

<210> SEQ ID NO 27
<211> LENGTH: 17
<212> TYPE: PRT
<213> ORGANISM: Homo sapiens
<220> FEATURE:
<223> OTHER INFORMATION: A12 VH CDR2 amino acid sequence

<400> SEQUENCE: 27

```
Ala Ile Ser Gly Ser Gly Gly Ser Thr Tyr Tyr Ala Asp Ser Val Lys
1               5                   10                  15

Gly
```

<210> SEQ ID NO 28
<211> LENGTH: 354
<212> TYPE: DNA
<213> ORGANISM: Homo sapiens
<220> FEATURE:
<223> OTHER INFORMATION: F4 & G11 VH domain nucleic acid sequence

<400> SEQUENCE: 28

```
gaggtgcagc tggtggagtc tgggggaggc ttggtacagc ctggggggtc cctgagactc    60
```

```
tcctgtgcag cctctggatt cacctttagc ggtagtcgta tgggctgggt ccgccaggct      120
ccagggaagg ggctggagtg ggtctcagct attaatgagg agggtggtca gacatactac      180
gcagactccg tgaagggccg gttcaccatc tccagagaca attccaagaa cacgctgtat      240
ctgcaaatga acagcctgag agccgaggac acggccgtat attactgtgc gaaacatccg      300
ccgcatcggc cgtttgacta ctggggccag ggaaccctgg tcaccgtctc gaga            354

<210> SEQ ID NO 29
<211> LENGTH: 118
<212> TYPE: PRT
<213> ORGANISM: Homo sapiens
<220> FEATURE:
<223> OTHER INFORMATION: F4 & G11 VH domain amino acid sequence

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Arg Met Gly Trp Val Arg Gln Ala Pro Gly Lys Gly Leu Glu Trp Val
        35                  40                  45

Ser Ala Ile Asn Glu Glu Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Pro His Arg Pro Phe Asp Tyr Trp Gly Gln Gly Thr
            100                 105                 110

Leu Val Thr Val Ser Arg
        115

<210> SEQ ID NO 30
<211> LENGTH: 327
<212> TYPE: DNA
<213> ORGANISM: Homo sapiens
<220> FEATURE:
<223> OTHER INFORMATION: F4 VL domain nucleic acid sequence

<400> SEQUENCE: 30
tcgtctgagc tgactcagga ccctgctgtg tctgtggcct tgggacagac agtcaggatc      60
acatgccaag agacagcctc agactttat tatgcaagct ggtaccagca gaagccagga      120
caggcccctg tacttgtcat ctatggtaaa tctagtcggc cctcagggat cccagaccga      180
ttctctggct ccagctcagg aaacacagct tccttgacca tcactgggc tcaggcggaa      240 gatgaggctg actattactg taactcctct catgggcccc gtaggcctgt ggtattcggc      300
ggagggacca agctgaccgt cctaggc                                          327

<210> SEQ ID NO 31
<211> LENGTH: 109
<212> TYPE: PRT
<213> ORGANISM: Homo sapiens
<220> FEATURE:
<223> OTHER INFORMATION: F4 VL domain amino acid sequence

<400> SEQUENCE: 31

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Leu Tyr Tyr Ala
```

```
                        20                  25                  30
Ser Trp Tyr Gln Gln Lys Pro Gly Gln Ala Pro Val Leu Val Ile Tyr
                    35                  40                  45

Gly Lys Ser Ser Arg Pro Ser Gly Ile Pro Asp Arg Phe Ser Gly Ser
                50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser His Gly Pro Arg Arg Pro
                    85                  90                  95

Val Val Phe Gly Gly Gly Thr Lys Leu Thr Val Leu Gly
                100                 105

<210> SEQ ID NO 32
<211> LENGTH: 11
<212> TYPE: PRT
<213> ORGANISM: Homo sapiens
<220> FEATURE:
<223> OTHER INFORMATION: F4 & G11 VL CDR1 amino acid sequence

<400> SEQUENCE: 32

Gln Gly Asp Ser Leu Arg Leu Tyr Tyr Ala Ser
1               5                   10

<210> SEQ ID NO 33
<211> LENGTH: 7
<212> TYPE: PRT
<213> ORGANISM: Homo sapiens
<220> FEATURE:
<223> OTHER INFORMATION: F4 VL CDR2 amino acid sequence

<400> SEQUENCE: 33

Gly Lys Ser Ser Arg Pro Ser
1               5

<210> SEQ ID NO 34
<211> LENGTH: 327
<212> TYPE: DNA
<213> ORGANISM: Homo sapiens
<220> FEATURE:
<223> OTHER INFORMATION: G11 VL domain nucleic acid sequence

<400> SEQUENCE: 34
tcgtctgagc tgactcagga ccctgctgtg tctgtggcct tgggacagac agtcaggatc      60
acatgccaag gagacagcct cagactttat tatgcaagct ggtaccagca gaagccagga     120
caggcccctg tacttgtcat ctatggtaaa acaaccggcc ctcagggat cccagaccga      180 ttctctggct ccagctcagg aaacacagct tccttgacca tcactgggc tcaggcggaa      240 gatgaggctg actattactg taactcctct catgggcccc gtaggcctgt ggtattcggc     300
ggagggacca agctgaccgt cctaggc                                         327

<210> SEQ ID NO 35
<211> LENGTH: 109
<212> TYPE: PRT
<213> ORGANISM: Homo sapiens
<220> FEATURE:
<223> OTHER INFORMATION: G11 VL domain amino acid sequence

<400> SEQUENCE: 35

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Leu Tyr Tyr Ala
                20                  25                  30
```

```
Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Ser His Gly Pro Arg Arg Pro
                 85                  90                  95

Val Val Phe Gly Gly Gly Thr Lys Leu Thr Val Leu Gly
            100                 105
```

<210> SEQ ID NO 36
<211> LENGTH: 42
<212> TYPE: DNA
<213> ORGANISM: Artificial sequence
<220> FEATURE:
<223> OTHER INFORMATION: Peptide linker nucleic acid sequence

<400> SEQUENCE: 36
ggtggaggcg gttcaggcgg aggtggctct ggcggtggcg ga         42

<210> SEQ ID NO 37
<211> LENGTH: 14
<212> TYPE: PRT
<213> ORGANISM: Artificial sequence
<220> FEATURE:
<223> OTHER INFORMATION: Peptide linker amino acid sequence

<400> SEQUENCE: 37

```
Gly Gly Gly Gly Ser Gly Gly Gly Gly Ser Gly Gly Gly Gly
 1               5                  10
```

<210> SEQ ID NO 38
<211> LENGTH: 45
<212> TYPE: DNA
<213> ORGANISM: Artificial sequence
<220> FEATURE:
<223> OTHER INFORMATION: Peptide linker nucleic acid sequence

<400> SEQUENCE: 38
ggtggaggcg gttcaggcgg aggtggttct ggcggtggcg gatcg      45

<210> SEQ ID NO 39
<211> LENGTH: 15
<212> TYPE: PRT
<213> ORGANISM: Artificial sequence
<220> FEATURE:
<223> OTHER INFORMATION: Peptide linker amino acid sequence

<400> SEQUENCE: 39

```
Gly Gly Gly Gly Ser Gly Gly Gly Gly Ser Gly Gly Gly Gly Ser
 1               5                  10                  15
```

<210> SEQ ID NO 40
<211> LENGTH: 45
<212> TYPE: DNA
<213> ORGANISM: Artificial sequence
<220> FEATURE:
<223> OTHER INFORMATION: Peptide linker nucleic acid sequence

<400> SEQUENCE: 40
tcttcctcat cgggtagtag ctcttccggc tcatcgtcca gcggc      45

<210> SEQ ID NO 41

```
<211> LENGTH: 15
<212> TYPE: PRT
<213> ORGANISM: Artificial sequence
<220> FEATURE:
<223> OTHER INFORMATION: Peptide linker amino acid sequence

<400> SEQUENCE: 41

Ser Ser Ser Ser Gly Ser Ser Ser Gly Ser Ser Ser Gly
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: Peptide linker amino acid sequence

<400> SEQUENCE: 42

Gly Ser Gly Ser Ala Gly Ser Gly Ser Ala Gly Ser Gly Ser Ala
1               5                   10                  15

<210> SEQ ID NO 43
<211> LENGTH: 15
<212> TYPE: PRT
<213> ORGANISM: Artificial sequence
<220> FEATURE:
<223> OTHER INFORMATION: Peptide linker amino acid sequence

<400> SEQUENCE: 43

Gly Gly Ser Gly Gly Gly Gly Ser Gly Gly Gly Gly Ser Gly Gly
1               5                   10                  15

<210> SEQ ID NO 44
<211> LENGTH: 354
<212> TYPE: DNA
<213> ORGANISM: Homo sapiens
<220> FEATURE:
<223> OTHER INFORMATION: New F4 & G11 VH domain nucleic acid sequence

<400> SEQUENCE: 44
gaggtgcagc tgtttggagtc tgggggaggc ttggtacagc ctgggggtc cctgagactc      60 tcctgtgcag cctctggatt cacctttagc ggtagtcgta tgggctgggt ccgccaggct     120
ccagggaagg gctggagtg gtctcagct attaatgagg agggtggtca gacatactac       180
gcagactccg tgaagggccg gttcaccatc tccagagaca attccaagaa cacgctgtat     240
ctgcaaatga acagcctgag agccgaagac acggccgtat attactgtgc gaaacatccg    300
ccgcatcggc cgtttgacta ctggggccag ggaaccctgg tcaccgtctc gagt          354

<210> SEQ ID NO 45
<211> LENGTH: 118
<212> TYPE: PRT
<213> ORGANISM: Homo sapiens
<220> FEATURE:
<223> OTHER INFORMATION: New F4 & G11 VH domain amino acid sequence

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Arg Met Gly Trp Val Arg Gln Ala Pro Gly Lys Gly Leu Glu Trp Val
        35                  40                  45

Ser Ala Ile Asn Glu Glu Gly Gly Gln Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Pro Pro His Arg Pro Phe Asp Tyr Trp Gly Gln Gly Thr
            100                 105                 110

Leu Val Thr Val Ser Ser
            115

<210> SEQ ID NO 46
<211> LENGTH: 324
<212> TYPE: DNA
<213> ORGANISM: Homo sapiens
<220> FEATURE:
<223> OTHER INFORMATION: New G11 VL domain nucleic acid sequence

<400> SEQUENCE: 46
tctgagctga ctcaggaccc tgctgtgtct gtggccttgg gacagacagt caggatcaca      60
tgccaaggag acagcctcag actttattat gcaagctggt accagcagaa gccaggacag     120
gcccctgtac ttgtcatcta tggtaaaaac aaccggccct cagggatccc agaccgattc     180
tctggctcca gctcaggaaa cacagcttcc ttgaccatca ctggggctca ggcggaagat     240
gaggctgact attactgtaa ctcctctcat gggccccgta ggcctgtggt attcggcgga     300
gggaccaagc tgaccgtcct aggc                                            324

<210> SEQ ID NO 47
<211> LENGTH: 108
<212> TYPE: PRT
<213> ORGANISM: Homo sapiens
<220> FEATURE:
<223> OTHER INFORMATION: New G11 VL domain amino acid sequence

<400> SEQUENCE: 47

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Leu Tyr Tyr Ala Ser
             20                  25                  30

Trp Tyr Gln Gln Lys Pro Gly Gln Ala Pro Val Leu Val Ile Tyr Gly
         35                  40                  45

Lys Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Ser His Gly Pro Arg Arg Pro Val
                 85                  90                  95

Val Phe Gly Gly Gly Thr Lys Leu Thr Val Leu Gly
            100                 105

<210> SEQ ID NO 48
<211> LENGTH: 118
<212> TYPE: PRT
<213> ORGANISM: Homo sapiens
<220> FEATURE:
<223> OTHER INFORMATION: New E10 VH domain amino acid sequence

<400> SEQUENCE: 48

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Ser
```

```
                20                  25                  30
Arg Met Gly Trp Val Arg Gln Ala Pro Gly Lys Gly Leu Glu Trp Val
            35                  40                  45

Ser Ala Ile Asn Glu Glu Gly Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Pro His Arg Pro Phe Asp Tyr Trp Gly Gln Gly Thr
            100                 105                 110

Leu Val Thr Val Ser Ser
            115

<210> SEQ ID NO 49
<211> LENGTH: 324
<212> TYPE: DNA
<213> ORGANISM: Homo sapiens
<220> FEATURE:
<223> OTHER INFORMATION: New 4A1-F16 & 3A1-D5 VL domain nucleotide
      sequence

<400> SEQUENCE: 49
tctgagctga ctcaggaccc tgctgtgtct gtggccttgg gacagacagt caggatcaca    60
tgccaaggag acagcctcag aagctattat gcaagctggt accagcagaa gccaggacag   120
gcccctgtac ttgtcatcta tggtaaaaac aaccggccct cagggatccc agaccgattc   180
tctggctcca gctcaggaaa cacagcttcc ttgaccatca ctggggctca ggcggaagat   240
gaggctgact attactgtaa ctcctctgtt tatactatgc cgcccgtggt attcggcgga   300
gggaccaagc tgaccgtcct aggc                                          324

<210> SEQ ID NO 50
<211> LENGTH: 108
<212> TYPE: PRT
<213> ORGANISM: Homo sapiens
<220> FEATURE:
<223> OTHER INFORMATION: New 4A1-F16 & 3A1-D5 VL domain amino acid
      sequence

<400> SEQUENCE: 50

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ser Val Tyr Thr Met Pro Pro Val
                85                  90                  95

Val Phe Gly Gly Gly Thr Lys Leu Thr Val Leu Gly
            100                 105

<210> SEQ ID NO 51
<211> LENGTH: 348
<212> TYPE: DNA
<213> ORGANISM: Homo sapiens
```

<220> FEATURE:
<223> OTHER INFORMATION: P12 VH domain nucleic acid sequence

<400> SEQUENCE: 51

```
gaggtgcagc tggtggagtc tgggggaggc ttggtacagc ctggggggtc cctgagactc      60
tcctgtgcag cctctggatt cacctttggc cagtattcta tgagctgggt ccgccaggct     120
ccagggaagg gctggagtg gtctcagct attacgggga ctggtggtga cacatactac      180
gcagactccg tggagggccg gttcaccatc tccagagaca attccaagaa cacgctgtat     240
ctgcaaatga acagcctgag agccgaggac acggccgtat attactgtgc gaaagggcgg     300
cggattttg actactgggg ccagggaacc ctggtcaccg tgtcgaga                    348
```

<210> SEQ ID NO 52
<211> LENGTH: 116
<212> TYPE: PRT
<213> ORGANISM: Homo sapiens
<220> FEATURE:
<223> OTHER INFORMATION: P12 VH domain amino acid sequence

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Gln Tyr
            20                  25                  30

Ser Met Ser Trp Val Arg Gln Ala Pro Gly Lys Gly Leu Glu Trp Val
        35                  40                  45

Ser Ala Ile Thr Gly Thr Gly Gly Glu Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Arg Ile Phe Asp Tyr Trp Gly Gln Gly Thr Leu Val
            100                 105                 110

Thr Val Ser Arg
        115
```

<210> SEQ ID NO 53
<211> LENGTH: 327
<212> TYPE: DNA
<213> ORGANISM: Homo sapiens
<220> FEATURE:
<223> OTHER INFORMATION: P12 and D11 VL domain nucleic acid sequence

<400> SEQUENCE: 53

```
tcgagtgagc tgactcagga ccctgctgtg tctgtggcct gggacagac agtcaggatc       60
acatgccaag agacagcct cagacggcag cctgcaagct ggtaccagca gaagccagga      120
caggcccctg tacttgtcat ctattataaa agctgcggc cctcagggat cccagaccga      180
ttctctggct ccagctcagg aaacacagct tccttgacca tcactgggc tcaggcggaa      240
gatgaggctg actattactg taactccttt tcgcccaagc cgaagcctgt ggtattcggc     300
ggagggacca agctgaccgt cctaggc                                          327
```

<210> SEQ ID NO 54
<211> LENGTH: 109
<212> TYPE: PRT
<213> ORGANISM: Homo sapiens
<220> FEATURE:
<223> OTHER INFORMATION: P12 and D11 VL domain amino acid sequence

<400> SEQUENCE: 54

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Arg Gln Pro Ala
            20                  25                  30

Ser Trp Tyr Gln Gln Lys Pro Gly Gln Ala Pro Val Leu Val Ile Tyr
        35                  40                  45

Tyr Lys Lys Leu Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Phe Ser Pro Lys Pro Lys Pro
                85                  90                  95

Val Val Phe Gly Gly Gly Thr Lys Leu Thr Val Leu Gly
                100                 105
```

<210> SEQ ID NO 55
<211> LENGTH: 348
<212> TYPE: DNA
<213> ORGANISM: Homo sapiens
<220> FEATURE:
<223> OTHER INFORMATION: D11 VH domain nucleic acid sequence

<400> SEQUENCE: 55

```
gaggtgcagc tggtggagtc tgggggaggc ttggtacagc ctgggggtc cctgagactc      60
tcctgtgcag cctctggatt caccttggc agctatgcca tgagctgggt ccgccaggct    120
ccagggaagg gctggagtg gtctcagct attagtggta gtggtggtag cacatactac     180
gcagactccg tggagggccg gttcaccatc tccagagaca attccaagaa cacgctgtat    240
ctgcaaatga acagcctgag agccgaggac acggccgtat attactgtgc gaaagggcgg   300
cggatttttg actactgggg ccagggaacc ctggtcaccg tgtcgaga                 348
```

<210> SEQ ID NO 56
<211> LENGTH: 116
<212> TYPE: PRT
<213> ORGANISM: Homo sapiens
<220> FEATURE:
<223> OTHER INFORMATION: D11 VH domain amino acid sequence

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Arg Ile Phe Asp Tyr Trp Gly Gln Gly Thr Leu Val
                100                 105                 110

Thr Val Ser Arg
            115
```

```
<210> SEQ ID NO 57
<211> LENGTH: 348
<212> TYPE: DNA
<213> ORGANISM: Homo sapiens
<220> FEATURE:
<223> OTHER INFORMATION: F4S VH domain nucleic acid sequence

<400> SEQUENCE: 57
gaggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtat attactgtgc gaaagggcgg    300 cggattttg actactgggg ccagggaacc ctggtcaccg tgtcgaga                  348

<210> SEQ ID NO 58
<211> LENGTH: 116
<212> TYPE: PRT
<213> ORGANISM: Homo sapiens
<220> FEATURE:
<223> OTHER INFORMATION: F4S VH domain amino acid sequence

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Arg Ile Phe Asp Tyr Trp Gly Gln Gly Thr Leu Val
            100                 105                 110

Thr Val Ser Arg
        115

<210> SEQ ID NO 59
<211> LENGTH: 327
<212> TYPE: DNA
<213> ORGANISM: Homo sapiens
<220> FEATURE:
<223> OTHER INFORMATION: F4S VL domain nucleic acid sequence

<400> SEQUENCE: 59
tcgtctgagc tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa acaaccggc cctcagggat cccagaccga     180
ttctctggct ccagctcagg aaacacagct tccttgacca tcactgggc tcaggcggaa    240 gatgaggctg actattactg taactccttt tcgcccaagc cgaagcctgt ggtattcggc   300
ggagggacca agctgaccgt cctaggc                                       327

<210> SEQ ID NO 60
```

```
<211> LENGTH: 109
<212> TYPE: PRT
<213> ORGANISM: Homo sapiens
<220> FEATURE:
<223> OTHER INFORMATION: F4S VL domain amino acid sequence

<400> SEQUENCE: 60

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Phe Ser Pro Lys Pro Lys Pro
                85                  90                  95

Val Val Phe Gly Gly Gly Thr Lys Leu Thr Val Leu Gly
            100                 105

<210> SEQ ID NO 61
<211> LENGTH: 5
<212> TYPE: PRT
<213> ORGANISM: Homo sapiens
<220> FEATURE:
<223> OTHER INFORMATION: P12 VH CDR1 amino acid sequence

<400> SEQUENCE: 61

Gln Tyr Ser Met Ser
1               5

<210> SEQ ID NO 62
<211> LENGTH: 5
<212> TYPE: PRT
<213> ORGANISM: Homo sapiens
<220> FEATURE:
<223> OTHER INFORMATION: D11 and F4S VH CDR1 amino acid sequence

<400> SEQUENCE: 62

Ser Tyr Ala Met Ser
1               5

<210> SEQ ID NO 63
<211> LENGTH: 17
<212> TYPE: PRT
<213> ORGANISM: Homo sapiens
<220> FEATURE:
<223> OTHER INFORMATION: P12 VH CDR2 amino acid sequence

<400> SEQUENCE: 63

Ala Ile Thr Gly Thr Gly Gly Glu Thr Tyr Tyr Ala Asp Ser Val Glu
1               5                   10                  15

Gly

<210> SEQ ID NO 64
<211> LENGTH: 17
<212> TYPE: PRT
<213> ORGANISM: Homo sapiens
<220> FEATURE:
<223> OTHER INFORMATION: D11 VH CDR2 amino acid sequence

<400> SEQUENCE: 64
```

Ala Ile Ser Gly Ser Gly Gly Ser Thr Tyr Tyr Ala Asp Ser Val Glu
1               5                   10                  15

Gly

<210> SEQ ID NO 65
<211> LENGTH: 17
<212> TYPE: PRT
<213> ORGANISM: Homo sapiens
<220> FEATURE:
<223> OTHER INFORMATION: F4S VH CDR2 amino acid sequence

<400> SEQUENCE: 65

Ala Ile Ser Gly Ser Gly Gly Ser Thr Tyr Tyr Ala Asp Ser Val Lys
1               5                   10                  15

Gly

<210> SEQ ID NO 66
<211> LENGTH: 7
<212> TYPE: PRT
<213> ORGANISM: Homo sapiens
<220> FEATURE:
<223> OTHER INFORMATION: P12, D11 and F4S VH CDR3 amino acid sequence

<400> SEQUENCE: 66

Gly Arg Arg Ile Phe Asp Tyr
1               5

<210> SEQ ID NO 67
<211> LENGTH: 11
<212> TYPE: PRT
<213> ORGANISM: Homo sapiens
<220> FEATURE:
<223> OTHER INFORMATION: P12 and D11 VL CDR1 amino acid sequence

<400> SEQUENCE: 67

Gln Gly Asp Ser Leu Arg Arg Gln Pro Ala Ser
1               5                   10

<210> SEQ ID NO 68
<211> LENGTH: 11
<212> TYPE: PRT
<213> ORGANISM: Homo sapiens
<220> FEATURE:
<223> OTHER INFORMATION: F4S VL CDR1 amino acid sequence

<400> SEQUENCE: 68

Gln Gly Asp Ser Leu Arg Ser Tyr Tyr Ala Ser
1               5                   10

<210> SEQ ID NO 69
<211> LENGTH: 7
<212> TYPE: PRT
<213> ORGANISM: Homo sapiens
<220> FEATURE:
<223> OTHER INFORMATION: P12 and D11 VL CDR2 amino acid sequence

<400> SEQUENCE: 69

Tyr Lys Lys Leu Arg Pro Ser
1               5

<210> SEQ ID NO 70
<211> LENGTH: 7
<212> TYPE: PRT
<213> ORGANISM: Homo sapiens
<220> FEATURE:
<223> OTHER INFORMATION: F4S VL CDR2 amino acid sequence

```
<400> SEQUENCE: 70

Gly Lys Asn Asn Arg Pro Ser
1               5

<210> SEQ ID NO 71
<211> LENGTH: 11
<212> TYPE: PRT
<213> ORGANISM: Homo sapiens
<220> FEATURE:
<223> OTHER INFORMATION: P12, D11 and F4S VL CDR3 amino acid sequence

<400> SEQUENCE: 71

Asn Ser Phe Ser Pro Lys Pro Lys Pro Val Val
1               5                   10

<210> SEQ ID NO 72
<211> LENGTH: 29
<212> TYPE: DNA
<213> ORGANISM: Artificial sequence
<220> FEATURE:
<223> OTHER INFORMATION: PCR oligonucleotide primer TnC-D BamHI ba

<400> SEQUENCE: 72
cgggatccgt tacagaagcc gaaccggaa                                     29

<210> SEQ ID NO 73
<211> LENGTH: 29
<212> TYPE: DNA
<213> ORGANISM: Artificial sequence
<220> FEATURE:
<223> OTHER INFORMATION: PCR oligonucleotide primer TnC-D BglII for

<400> SEQUENCE: 73
cgggatccgt tacagaagcc gaaccggaa                                     29

<210> SEQ ID NO 74
<211> LENGTH: 60
<212> TYPE: DNA
<213> ORGANISM: Artificial sequence
<220> FEATURE:
<223> OTHER INFORMATION: PCR oligonucleotide primer mmTnC-A1 EcoBa

<400> SEQUENCE: 74
agaattcatt aaagaggaga aattaactat gagaggatcc tccacggaag aagtgccttc   60

<210> SEQ ID NO 75
<211> LENGTH: 29
<212> TYPE: DNA
<213> ORGANISM: Artificial sequence
<220> FEATURE:
<223> OTHER INFORMATION: PCR oligonucleotide primer mmTnC-A1 BglFo

<400> SEQUENCE: 75
tgagatcttg tccctgtgga ggtctcggc                                     29

<210> SEQ ID NO 76
<211> LENGTH: 5
<212> TYPE: PRT
<213> ORGANISM: Artificial sequence
<220> FEATURE:
<223> OTHER INFORMATION: Peptide linker motif

<400> SEQUENCE: 76

Gly Gly Gly Gly Ser
1               5
```

```
<210> SEQ ID NO 77
<211> LENGTH: 5
<212> TYPE: PRT
<213> ORGANISM: Artificial sequence
<220> FEATURE:
<223> OTHER INFORMATION: Peptide linker motif

<400> SEQUENCE: 77

Ser Ser Ser Ser Gly
1               5

<210> SEQ ID NO 78
<211> LENGTH: 5
<212> TYPE: PRT
<213> ORGANISM: Artificial sequence
<220> FEATURE:
<223> OTHER INFORMATION: Peptide linker motif

<400> SEQUENCE: 78

Gly Ser Gly Ser Ala
1               5

<210> SEQ ID NO 79
<211> LENGTH: 5
<212> TYPE: PRT
<213> ORGANISM: Artificial sequence
<220> FEATURE:
<223> OTHER INFORMATION: Peptide linker motif

<400> SEQUENCE: 79

Gly Gly Ser Gly Gly
1               5

<210> SEQ ID NO 80
<211> LENGTH: 324
<212> TYPE: DNA
<213> ORGANISM: Homo sapiens
<220> FEATURE:
<223> OTHER INFORMATION: New E10 & A12 VL domain nucleotide sequence

<400> SEQUENCE: 80
tctgagctga ctcaggaccc tgctgtgtct gtggccttgg gacagacagt caggatcaca    60
tgccaaggag acagcctcag aagctattat gcaagctggt accagcagaa gccaggacag   120
gcccctgtac ttgtcatcta tggtaaaaac aaccggccct cagggatccc agaccgattc   180
tctggctcca gctcaggaaa cacagcttcc ttgaccatca ctggggctca ggcggaagat   240
gaggctgact attactgtaa ctcctctcat gggccccgta ggcctgtggt attcggcgga   300
gggaccaagc tgaccgtcct aggc                                          324

<210> SEQ ID NO 81
<211> LENGTH: 108
<212> TYPE: PRT
<213> ORGANISM: Homo sapiens
<220> FEATURE:
<223> OTHER INFORMATION: New E10 & A12 VL domain amino acid sequence

<400> SEQUENCE: 81

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
```

```
            50                  55                  60
Ser Gly Asn Thr Ala Ser Leu Thr Ile Thr Gly Ala Gln Ala Glu Asp
 65                  70                  75                  80

Glu Ala Asp Tyr Tyr Cys Asn Ser Ser His Gly Pro Arg Arg Pro Val
                 85                  90                  95

Val Phe Gly Gly Gly Thr Lys Leu Thr Val Leu Gly
                100                 105

<210> SEQ ID NO 82
<211> LENGTH: 324
<212> TYPE: DNA
<213> ORGANISM: Homo sapiens
<220> FEATURE:
<223> OTHER INFORMATION: New F4 VL domain nucleic acid sequence

<400> SEQUENCE: 82
tctgagctga ctcaggaccc tgctgtgtct gtggccttgg gacagacagt caggatcaca        60
tgccaaggag acagcctcag actttattat gcaagctggt accagcagaa gccaggacag       120
gcccctgtac ttgtcatcta tggtaaatct agtcggccct cagggatccc agaccgattc       180
tctggctcca gctcaggaaa cacagcttcc ttgaccatca ctggggctca gcggaagat        240 gaggctgact attactgtaa ctcctctcat gggccccgta ggcctgtggt attcggcgga       300
gggaccaagc tgaccgtcct aggc                                              324

<210> SEQ ID NO 83
<211> LENGTH: 108
<212> TYPE: PRT
<213> ORGANISM: Homo sapiens
<220> FEATURE:
<223> OTHER INFORMATION: New F4 VL domain amino acid sequence

<400> SEQUENCE: 83

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Leu Tyr Tyr Ala Ser
                20                  25                  30

Trp Tyr Gln Gln Lys Pro Gly Gln Ala Pro Val Leu Val Ile Tyr Gly
             35                  40                  45

Lys Ser Ser Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Ser His Gly Pro Arg Arg Pro Val
                 85                  90                  95

Val Phe Gly Gly Gly Thr Lys Leu Thr Val Leu Gly
                100                 105

<210> SEQ ID NO 84
<211> LENGTH: 29
<212> TYPE: DNA
<213> ORGANISM: Artificial sequence
<220> FEATURE:
<223> OTHER INFORMATION: PCR oligonucleotide TnC-A1 BamHI ba

<400> SEQUENCE: 84
cgggatcctc cactgaacaa gcccctgag                                          29

<210> SEQ ID NO 85
<211> LENGTH: 29
<212> TYPE: DNA
```

```
<213> ORGANISM: Artificial sequence
<220> FEATURE:
<223> OTHER INFORMATION: PCR oligonucleotide TnC-A1 BglII for

<400> SEQUENCE: 85
ggagatcttt ccctgtgga ggcctcagc                                29

<210> SEQ ID NO 86
<211> LENGTH: 26
<212> TYPE: DNA
<213> ORGANISM: Artificial sequence
<220> FEATURE:
<223> OTHER INFORMATION: PCR oligonucleotide LMB3 long ba

<400> SEQUENCE: 86
caggaaacag ctatgaccat gattac                                  26

<210> SEQ ID NO 87
<211> LENGTH: 54
<212> TYPE: DNA
<213> ORGANISM: Artificial sequence
<220> FEATURE:
<223> OTHER INFORMATION: PCR oligonucleotide DP47CDR1mut for
<220> FEATURE:
<221> NAME/KEY: misc_feature
<222> LOCATION: 23, 24, 26, 27, 29, 30
<223> OTHER INFORMATION: n is a or g or c or t

<400> SEQUENCE: 87
agcctggcgg acccagctcg cmnnmnnmnn gctaaaggtg aatccagagg ctgc    54

<210> SEQ ID NO 88
<211> LENGTH: 21
<212> TYPE: DNA
<213> ORGANISM: Artificial sequence
<220> FEATURE:
<223> OTHER INFORMATION: Primer DP47CDR1 ba

<400> SEQUENCE: 88
gagctgggtc cgccaggctc c                                       21

<210> SEQ ID NO 89
<211> LENGTH: 30
<212> TYPE: DNA
<213> ORGANISM: Artificial sequence
<220> FEATURE:
<223> OTHER INFORMATION: Primer fdseq long for

<400> SEQUENCE: 89
gacgttagta aatgaatttt ctgtatgagg                              30

<210> SEQ ID NO 90
<211> LENGTH: 58
<212> TYPE: DNA
<213> ORGANISM: Artificial sequence
<220> FEATURE:
<223> OTHER INFORMATION: PCR oligonucleotide DP47CDR1 for
<220> FEATURE:
<221> NAME/KEY: misc_feature
<222> LOCATION: 27, 28, 30, 31, 33, 34
<223> OTHER INFORMATION: n is a or g or c or t

<400> SEQUENCE: 90
ctggagcctg gcggacccag ctcatmnnmn nmnngctaaa ggtgaatcca gaggctgc  58

<210> SEQ ID NO 91
<211> LENGTH: 19
<212> TYPE: DNA
```

```
<213> ORGANISM: Artificial sequence
<220> FEATURE:
<223> OTHER INFORMATION: PCR oligonucleotide DP47CDR1 ba

<400> SEQUENCE: 91
tgggtccgcc aggctccag                                              19

<210> SEQ ID NO 92
<211> LENGTH: 64
<212> TYPE: DNA
<213> ORGANISM: Artificial sequence
<220> FEATURE:
<223> OTHER INFORMATION: PCR oligonucleotide DP47CDR2 for
<220> FEATURE:
<221> NAME/KEY: misc_feature
<222> LOCATION: 29, 30, 38, 39, 41, 42, 44, 45
<223> OTHER INFORMATION: n is a or g or c or t

<400> SEQUENCE: 92
gcccttcacg gagtctgcgt agtatgtmnn accaccmnnm nnmnnaatag ctgagaccca      60
ctcc                                                              64

<210> SEQ ID NO 93
<211> LENGTH: 27
<212> TYPE: DNA
<213> ORGANISM: Artificial sequence
<220> FEATURE:
<223> OTHER INFORMATION: PCR oligonucleotide DPR47CDR2 ba

<400> SEQUENCE: 93
acatactacg cagactccgt gaagggc                                     27
```